(12) United States Patent
Kassis et al.

(10) Patent No.: US 9,707,239 B2
(45) Date of Patent: Jul. 18, 2017

(54) COMPOUNDS THAT MODULATE OXIDATIVE STRESS

(71) Applicant: vTv Therapeutics LLC, High Point, NC (US)

(72) Inventors: Jareer Nabeel Kassis, Colfax, NC (US); Otis Clinton Attucks, Winston-Salem, NC (US); Matthew J. Kostura, Hillsborough, NC (US)

(73) Assignee: vTv Therapeutics LLC, High Point, NC (US)

( * ) Notice: Subject to any disclaimer, the term of this patent is extended or adjusted under 35 U.S.C. 154(b) by 0 days.

(21) Appl. No.: 15/247,256

(22) Filed: Aug. 25, 2016

(65) Prior Publication Data

US 2017/0056413 A1  Mar. 2, 2017

Related U.S. Application Data

(60) Division of application No. 13/894,922, filed on May 15, 2013, now Pat. No. 9,447,468, which is a continuation of application No. PCT/US2012/020459, filed on Jan. 6, 2012.

(60) Provisional application No. 61/430,927, filed on Jan. 7, 2011, provisional application No. 61/545,091, filed on Oct. 7, 2011, provisional application No. 61/563,174, filed on Dec. 28, 2011.

(51) Int. Cl.
| | |
|---|---|
| *A61K 38/43* | (2006.01) |
| *C12Q 1/68* | (2006.01) |
| *A61K 31/56* | (2006.01) |
| *A61K 31/426* | (2006.01) |
| *A61K 31/427* | (2006.01) |
| *A61K 31/428* | (2006.01) |
| *A61K 31/4709* | (2006.01) |

(52) U.S. Cl.
CPC ............ *A61K 31/56* (2013.01); *A61K 31/426* (2013.01); *A61K 31/427* (2013.01); *A61K 31/428* (2013.01); *A61K 31/4709* (2013.01); *C12Q 1/6883* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,288,374 B2 | 10/2007 | Pincemail et al. | |
| 7,306,905 B2 | 12/2007 | Ron et al. | |
| 8,759,535 B2 | 6/2014 | Mjalli et al. | |
| 9,447,468 B2 * | 9/2016 | Kassis | C12Q 1/6883 |
| 2009/0042980 A1 | 2/2009 | Lipton et al. | |
| 2010/0304384 A1 | 12/2010 | Valdivieso Amate et al. | |
| 2011/0201604 A1 | 8/2011 | Mjalli et al. | |
| 2011/0262570 A1 | 10/2011 | Finlay et al. | |
| 2012/0071505 A1 | 3/2012 | Gaddam et al. | |
| 2014/0200212 A1 | 7/2014 | Mjalli et al. | |

FOREIGN PATENT DOCUMENTS

| | | |
|---|---|---|
| EP | 2392674 A2 | 12/2011 |
| WO | WO 2007/005879 A2 | 1/2007 |
| WO | WO 2007/089857 A2 | 8/2007 |
| WO | WO 2009/146216 A2 | 12/2009 |
| WO | WO 2010/107955 A2 | 9/2010 |
| WO | WO 2011/103018 | 8/2011 |

OTHER PUBLICATIONS

Sethe et al., "Aging of mesenchymal stem cells" 5 Ageing Research Reviews 91-116 (2006).*
Alam et al., "How Many Transcription Factors Does It Take to Turn on the Heme Oxygenase-1 Gene?" Am J Respir Cell Mol Biol vol. 36:166-174 (2007).
Attucks OC, et al. (2014) Induction of Heme Oxygenase I (HMOX1) by HPP-4382: A Novel Modulator of Bach1 Activity. PLoS ONE 9(7): e101044. doi:10.1371/journal.pone.0101044.
Baker et al., "Microtiter Plate Assay for the Measurement of Glutathione and Glutathione Disulfide in Large Numbers of Biological Samples," Analytical Biochemistry 190:360-365 (1990).
Camera et al., "Analytical methods to investigate glutathione and related compounds in biological and pathological processes," Journal of Chromatography B 781:181-206 (2002).
Goven et al., "Altered Nrf2/Keap1-Bach1 equilibrium in pulmonary emphysema," Thorax 63:916-924 (2008).
Han et al., "Oxidative Preconditioning and Apoptosis in L-cells: Roles of Protein Kinase B and Mitogen-Activated Protein Kinases," The Journal of Biological Chemistry 276(28):26357-26364 (2001).
Hansen et al., "Nuclear and Mitochondrial Compartmentation of Oxidative Stress and Redox Signaling" 46 Annual Review of Pharmacology and Toxicology 215-234 (2006).
He et al., "Effect of p479(phox) gene deletion on ROS production and oxygen sensing in mouse carotid body chemoreceptor cells," American Journal of Physiology—Lung Cellular and Molecular Physiology 289(6):L916-L924 (2005).
Honda et al., "Synthetic Oleanane and Ursane Triterpenoids with Modified Rings A and C: A Series of Highly Active Inhibitors of Nitric Oxide Production in Mouse Macrophages," Journal of Medicinal Chemistry 43(22):4233-4246 (2000).
Inoguchi et al., "High Glucose Level and Free Fatty Acid Stimulate Reactive Oxygen Species Production Through Protein Kinase C-Dependent Activation of NAD(P)H Oxidase in Cultured Vascular Cells," Diabetes 49:1939-1945 (2000).
International Search Report and Written Opinion for related PCT Application No. PCT/US2012/020459 mailed Jul. 6, 2012.
Jones, "Redox Potential of GSH/GSSG Couple: Assay and Biological Significance," Methods in Enzymology 348:93-112 (2002).

(Continued)

*Primary Examiner* — Nancy J Leith
(74) *Attorney, Agent, or Firm* — Samuel B. Rollins

(57) ABSTRACT

The present invention provides methods of identifying compounds that selectively induce an oxidative stress response in a biological sample. The present invention further provides methods of treating a subject having a disease associated with oxidative stress using compounds that selectively induce an oxidative stress response in the subject. The invention further provides methods of selectively inducing an oxidative stress response in a cell.

7 Claims, 13 Drawing Sheets

(56) References Cited

OTHER PUBLICATIONS

Kostura et al., "Novel Bach1 Modulators Increase HMOX1 and Suppress Hypertension in the Goldblatt Model of Renovascular Hypertension," American Heart Association Scientific Sessions, Nov. 2013, Poster.
Li et al., "Treatment of Obese Diabetic Mice With a Heme Oxygenase Inducer Reduces Visceral and Subcutaneous Adiposity, Increases Adiponectin Levels, and Improves Insulin Sensitivity and Glucose Tolerance," Diabetes 57(6):1526-1535 (2008).
MacLeod et al., "Characterization of the cancer chemopreventive NRF2-dependent gene battery in human keratinocytes: demonstration that the KEAP1-NRF2 pathway, and not the BACH1-NRF2 pathway, controls cytoprotection against electrophiles as well as redox-cycling compounds," Carcinogenesis 30(9):1571-1580 (2009).
Martindale et al., "Cellular Response to Oxidative Stress: Signaling for Suicide and Survival," Journal of Cellular Physiology 192:1-15 (2002).
Otterbein et al., "Heme oxygenase: colors of defense against cellular stress," American Journal of Physiology—Lung Cellular and Molecular Physiology 279:L1029-L1037 (2000).
Panomics catalog listing for Plex Set 11307 (Human)—Sep. 30, 2014.
Product Insert for QuantiGene Plex 2.0, Plex Set 10028 (Human)—Jun. 18, 2008.
Product Insert for QuantiGene Plex 2.0, Plex Set 11237 (Human)—Nov. 13, 2008.
Reichard et al., "Heme oxygenase-1 induction by NRF2 requires inactivation of the transcriptional repressor BACH1," Nucleic Acids Research 35(21):7074-7086 (2007).
Sakoda et al., "Regulation of heme oxgenase-1 by transcription factor Bach1 in the mouse brain," Neuroscience Letters 440:160-165 (2008).
Schipper et al., "Heme oxygenase-1 and neurodegeneration: expanding frontiers of engagement," Journal of Neurochemistry 110(2):469-485 (2009).
Shan et al., "Role of Bach1 and Nrf2 in up-regulation of the heme oxygenase-1 gene by cobalt protoporphyrin," The FASEB Journal E2258-E2267/E2651-2653 (2006).
Siafakas et al., "Growth arrest and DNA damage-45 alpha (GADD45alpha)," The International Journal of Biochemistry & Cell Biology 41:986-989 (2009).
Sun et al., "Hemoprotein Bach1 regulates enhancer availability of heme oxygenase-1 gene," The EMBO Journal 21(19):5216-5224 (2002).
Taguchi et al., "Genetic Analysis of Cytoprotective Functions Supported by Graded Expression of Keap1," Molecular and Cellular Biology 30(12):3016-3026 (2010).
Zhang et al., "Enhanced expression of Nrf2 in mice attenuates the fatty liver produced by a methionine- and choline-deficient diet," Toxicology and Applied Pharmacology 245:326-334 (2010).

\* cited by examiner

COMPOUNDS THAT MODULATE OXIDATIVE STRESS

FIELD OF THE INVENTION

The present invention provides methods of identifying compounds that selectively induce an oxidative stress response in a biological sample, methods of treating a subject having a disease associated with oxidative stress using compounds that selectively induce an oxidative stress response in the subject methods of selectively inducing an oxidative stress response in a cell.

BACKGROUND OF THE INVENTION

Oxidative stress represents an imbalance between cellular reactive oxygen species (ROS) production and cellular responses to ROS such as degrading ROS species and producing endogenous anti-oxidant molecules. When left unchecked, increased ROS levels in a cell can result in damage to components such as lipids, proteins, polysaccharides, and DNA. Prolonged oxidative stress is also linked to chronic diseases that affect nearly every major organ system. For example, prolonged activation of oxidative stress is implicated in the onset or progression of disease states such as neurodegenerative diseases, lung diseases, cardiovascular diseases, renal diseases, diabetes, inflammatory pain, and cancer. Accordingly, strategies to mitigate oxidative stress are desirable for a number of therapeutic settings.

Heme oxygenase (HMOX1) is an enzyme that degrades heme to produce the cytoprotective molecules iron, biliverdin, and carbon monoxide, which have antiapoptotic, anti-inflammatory, and antioxidant effects. HMOX1 expression is ubiquitously induced in mammalian tissues in response to diverse stressors, such as ultraviolet radiation, endotoxins, heavy metals, and oxidative stress. HMOX1 expression is also induced in numerous disease and injury states, such as atherosclerosis, ischemia, hypertension, chronic obstructive lung disease, hyperoxia-induced lung injury, acute renal failure, and cancer (see, e.g., Otterbein and Choi, *Am. J. Physiol. Lung Cell. Mol. Physiol.* 279:L1029-L1037 (2000)). It has been shown that the regulation of HMOX1 protein levels leads to changes in pathophysiology in disease models. For example, mice that are deficient for HMOX1 exhibit increased severity of disease symptoms such as pancreatitis in models of diabetes, increased intimal thickening in models of vascular injury, and increased plaque formation in apolipoprotein E (APOE) deficient mice; adenoviral gene transfer of HMOX1 ameliorates pathology in animal models of hyperoxia induced lung injury, islet transplantation survival, ischemia reperfusion in rats and mice, and in atherosclerotic lesion formation in APOE deficient mice; and pharmacological regulation of HMOX1 leads to amelioration of pathology in animal models of cardiovascular disease. The combination of epidemiological association studies, genetic models, and animal pharmacology findings support a protective role for HMOX1 and indicate that therapeutic elevation of HMOX1 in disease settings can be adaptive and protective.

BRIEF SUMMARY OF THE INVENTION

In one aspect, the present invention provides methods of identifying compounds that decrease oxidative stress by selectively inducing oxidative stress response in a biological sample. In some embodiments, the method comprises:

(a) contacting the biological sample with one or more compounds;

(b) determining whether the one or more compounds induce an oxidative stress response in the biological sample, wherein induction of the oxidative stress response comprises inducing expression of an oxidative stress-responsive gene that is responsive to transcription factor Nrf2;

(c) determining whether the one or more compounds activate a cellular stress response in the biological sample, wherein activation of the cellular stress response comprises inducing expression of a cellular stress gene other than an oxidative stress-responsive gene, wherein the cellular stress gene is an ER stress-responsive gene, a genotoxic stress-responsive gene, a heat stress-responsive gene, or a cold stress-responsive gene; and (d) selecting for the one or more compounds that induce the oxidative stress response but do not significantly activate the cellular stress response in the biological sample; wherein the one or more compounds that are selected for are identified as decreasing oxidative stress by selectively inducing oxidative stress response.

In some embodiments, step (d) comprises selecting for the one or more compounds that induce expression of the oxidative stress-responsive gene in the biological sample by at least about two-fold.

In some embodiments, step (b) comprises determining whether the one or more compounds induce expression of HMOX1 and at least one other oxidative stress-responsive gene, and step (d) comprises selecting for the one or more compounds that induce expression of HMOX1 and the at least one other oxidative stress-responsive gene.

In some embodiments, the method further comprises (c)(1) determining whether the one or more compounds activate NF-κB in the biological sample, and step (d) further comprises selecting for the one or more compounds that do not significantly activate NF-κB in the biological sample.

In some embodiments, the method further comprises (c)(2) determining whether the one or more compounds increase reactive oxygen species (ROS) production in the biological sample, and step (d) further comprises selecting for the one or more compounds that do not significantly increase ROS production in the biological sample.

In some embodiments, the method further comprises (c)(3) determining whether the one or more compounds decrease the level of glutathione in the biological sample, and step (d) further comprises selecting for the one or more compounds that do not significantly decrease the level of glutathione in the biological sample.

In another aspect, the present invention provides structurally related analogs of a selected-for compound.

In another aspect, the present invention provides methods of administering to an animal a structurally related analog of a selected-for compound. In some embodiments, the method comprises determining whether the analog has an EC50 less than or equal to Cobalt Protoporphyrin (CoPP) for inducing expression of the oxidative stress-responsive gene. In some embodiments, the method comprises determining the oral bioavailability of the analog. In some embodiments, the method comprises determining the metabolic profile of the analog.

In yet another aspect, the present invention provides methods of treating a subject having a disease associated with oxidative stress. In some embodiments, the method comprises:

(a) identifying the subject having the disease associated with oxidative stress; and
(b) administering to the subject a compound that decreases oxidative stress by selectively inducing oxidative stress response in the subject, wherein the compound induces expression of an oxidative stress-responsive gene that is responsive to transcription factor Nrf2, but does not significantly induce expression of a cellular stress gene other than an oxidative stress-responsive gene and does not significantly increase production of reactive oxygen species in the subject; thereby treating the subject having the disease.

In some embodiments, the compound induces expression of the oxidative stress-responsive gene heme oxygenase 1 (HMOX1).

In another aspect, the present invention provides methods of selectively inducing an oxidative stress response in a cell, the method comprising: contacting a cell with a selective heme oxygenase 1 (HMOX1) inducer, where the HMOX1 inducer is a non-naturally-occurring organic molecule.

In still another aspect, the present invention provides methods of reducing ischemic damage in a subject. In some embodiments, the method comprises:
(a) identifying the subject having ischemic damage; and
(b) administering to the subject a compound that decreases oxidative stress by selectively inducing oxidative stress response in the subject, wherein the compound induces expression of an oxidative stress-responsive gene that is responsive to transcription factor Nrf2, but does not significantly induce expression of a cellular stress gene other than an oxidative stress-responsive gene and does not significantly increase production of reactive oxygen species in the subject; thereby reducing ischemic damage in the subject.

In yet another aspect, the present invention provides methods of reducing inflammation associated with transplantation in a subject. In some embodiments, the method comprises:
(a) identifying the subject having inflammation associated with transplantation; and
(b) administering to the subject a compound that decreases oxidative stress by selectively inducing oxidative stress response in the subject, wherein the compound induces expression of an oxidative stress-responsive gene that is responsive to transcription factor Nrf2, but does not significantly induce expression of a cellular stress gene other than an oxidative stress-responsive gene and does not significantly increase production of reactive oxygen species in the subject; thereby reducing the inflammation associated with transplantation in the subject.

In yet another aspect, the present invention provides methods of improving graft viability in a graft recipient. In some embodiments, the method comprises:
(a) identifying the graft recipient; and
(b) administering to the graft recipient a compound that decreases oxidative stress by selectively inducing oxidative stress response in the graft recipient, wherein the compound induces expression of an oxidative stress-responsive gene that is responsive to transcription factor Nrf2, but does not significantly induce expression of a cellular stress gene other than an oxidative stress-responsive gene and does not significantly increase production of reactive oxygen species in the graft recipient; thereby improving graft viability in the graft recipient.

In still another aspect, the present invention provides methods of maintaining an arteriovenous fistula in a subject. In some embodiments, the method comprises:
(a) identifying the subject having the arteriovenous fistula; and
(b) administering to the subject a compound that decreases oxidative stress by selectively inducing oxidative stress response in the subject, wherein the compound induces expression of an oxidative stress-responsive gene that is responsive to transcription factor Nrf2, but does not significantly induce expression of a cellular stress gene other than an oxidative stress-responsive gene and does not significantly increase production of reactive oxygen species in the subject; thereby maintaining the arteriovenous fistula in the subject.

In still another aspect, the present invention provides for the use of a compound as described herein (e.g., a compound identified according to any of the methods described herein) for the preparation of a medicament for the treatment of a disease or condition associated with oxidative stress (e.g., fibrotic disease, neurodegenerative disease, cardiovascular disease, renal disease, inflammatory disease, liver disease, eye disease, thyroid disease, skin disease, viral infection, osteoporosis, or diabetes), or for the reduction of ischemic damage, or for the reduction of inflammation associated with transplantation, or for the improvement of graft viability, or for the maintenance of an arteriovenous fistula.

BRIEF DESCRIPTION OF THE DRAWINGS

FIG. 3A. The screening hits Compound 13, Compound 14, and Compound 15 show little increase in ROS production. FIG. 3B. Derivatives of Compound 13 (Compound 2, Compound 3, Compound 4, and Compound 5) show no demonstrable increase in ROS production.

As shown in FIG. 4, HMOX1 induction by ROS generators such as celestrol, curcumin, Compound 14, and Compound 15 is fully suppressed in the presence of NAC, whereas Compound 13 still induces HMOX1 expression in the presence of NAC.

As shown in FIG. 5, the induction of HMOX1 mRNA through exposure of NHLF cells to Compound 13, Compound 14, or Compound 15 requires Nrf2 for full induction of HMOX1 mRNA.

As shown in FIG. 6, the induction of HMOX1 mRNA through exposure of NHLF cells to Compound 13 and its derivatives, Compound 4 and Compound 8, behaves similarly to CoPP induction, indicating that the test compounds do not affect Keap1-Nrf2 activity.

As shown in FIG. 7, ectopic expression of human Bach1 suppresses basal activation of the luciferase reporter in a regulated manner. The tool compound and Bach1 modulator CoPP can overcome this repression, as can Compound 7, demonstrating that the oxidative stress modulators can affect Bach1 activity directly.

DETAILED DESCRIPTION OF THE INVENTION

I. Definitions

Figure 1:
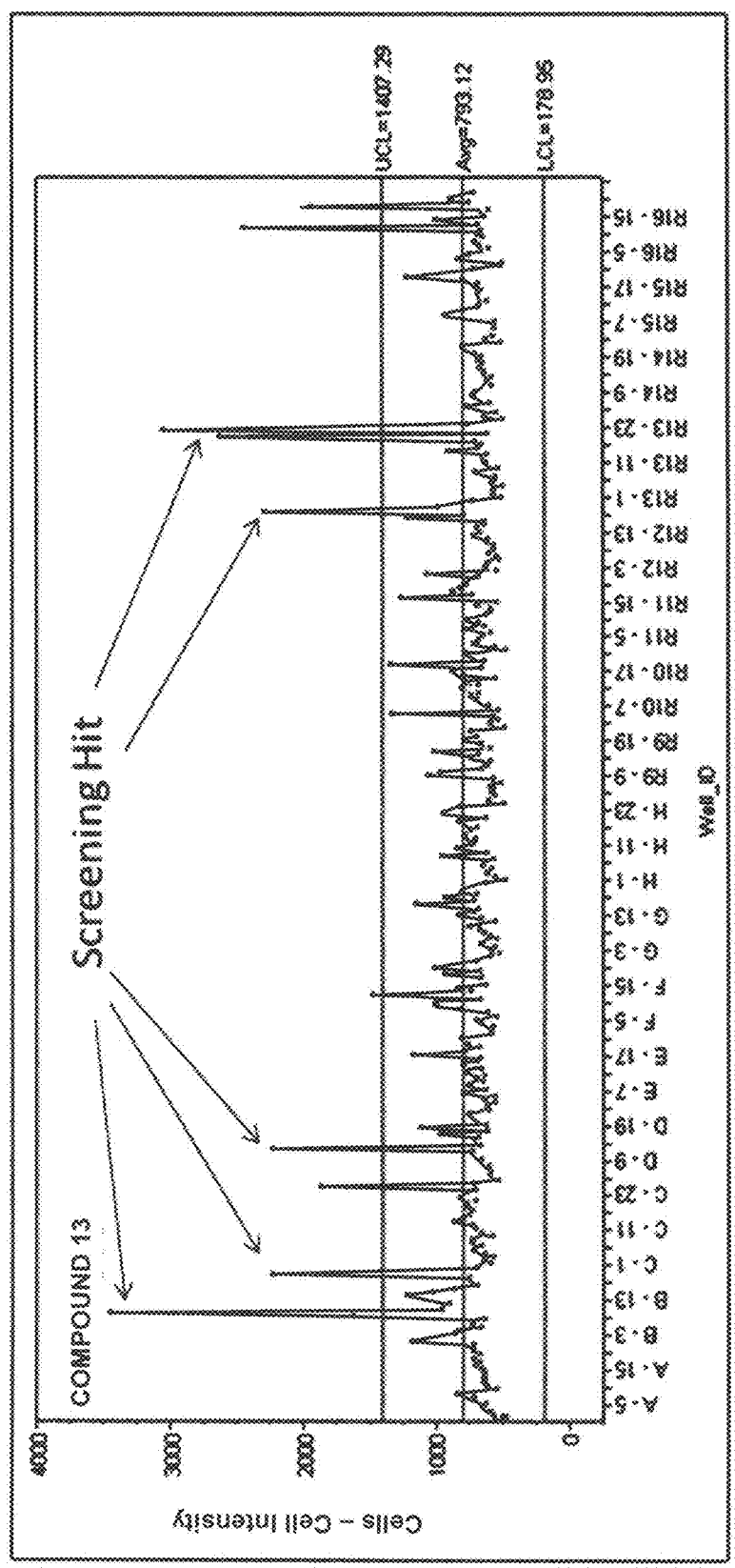
FIG. 1. Example of HMOX1 protein expression data as measured using immunofluorescence. Screening hits, such as Compound 13 shown on the left side of the figure, are those compounds that have a value significantly greater than the upper confidence limit (UCL) of the assay.

As used herein, the term "oxidative stress response" refers to a physiological response in a biological sample (e.g., a cell) to an imbalance between the production of reactive oxygen species (ROS), chemically reactive molecules comprising oxygen ions including but not limited to, superoxide anion ($.O_2^-$), hydroxyl anion (.OH), peroxynitrite ($OONO^-$), nitric oxide ($NO^-$), and hydrogen peroxide ($H_2O_2$), and the cellular regulation of ROS through enzymes, antioxidants, and other compounds that facilitate ROS breakdown and keep the cell in a state of redox balance. In some embodiments, the physiological response to oxidative stress comprises the upregulation of genes encoding proteins that have cytoprotective activities as described herein.

As used herein, the term "oxidative stress-responsive gene" refers to a nucleic acid encoding a polypeptide that is cytoprotective in the presence of oxidative stress. In some embodiments, an oxidative stress-responsive gene is a gene that is induced by the transcription factor Nrf2 (i.e., transcription of the gene is activated by Nrf2).

Oxidative stress-responsive genes recited herein refer to genes, including polymorphic variants, alleles, mutants, and interspecies homologs, that: (1) encode a polypeptide having an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) encode a polypeptide that specifically binds to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; or (4) have a nucleic acid sequence that has greater than about 60% nucleotide sequence identity, 65%, 70%, 75%, 80%, 85%, 90%, 91%, 92%, 93%, 94%, 95%, 96%, 97%, 98% or 99% or higher nucleotide sequence identity, preferably over a region of at least about 10, 15, 20, 25, 50, 100, 200, 500, 1000, or more nucleotides, to a reference nucleic acid sequence. A polynucleotide or polypeptide sequence is typically from an animal including, but not limited to, mammals (e.g., a human or a non-human primate; a rodent, e.g., rat, mouse, hamster; cow, pig, horse, sheep, or any other mammal), fish (e.g., zebrafish), and invertebrate animals (e.g., *C. elegans* and *Drosophila*). The nucleic acids and proteins of the invention include both naturally occurring or recombinant molecules. Truncated and alternatively spliced forms of these molecules are included in the definition.

Oxidative stress-responsive genes of the present invention may be identified by gene name, e.g., heme oxygenase 1; gene symbol, e.g., Hmox1; Entrez Gene ID, e.g., 15368; Genbank accession number, e.g., $NM_{13}$ 010442.2; or the like. It is understood that all of these identifiers reference the same biomarker and thus are equivalent. Oxidative stress-responsive genes of the invention are identified in Table 1 below, and include: Psmb5 (proteasome subunit, beta type 5; Gene ID 19173); Atox1 (ATX (antioxidant protein 1) homolog 1 (yeast); Gene ID 11927); Gstm1 (glutathione S-transferase, mu 1; Gene ID 14862); Coq7 (demethyl-Q 7; Gene ID 12850); Als2 (amyotrophic lateral sclerosis 2 (juvenile) homolog (human); Gene ID 74018); Gsta1 (glutathione S-transferase, alpha 1 (Ya); Gene ID 14857); Gsta2 (glutathione S-transferase, alpha 2 (Yc2); Gene ID 14858); Jak2 (Janus kinase 2; Gene ID 16452); Txnrd1 (thioredoxin reductase 1; Gene ID 50493); Gsr (glutathione reductase; Gene ID 14782); Nqo1 (NAD(P)H dehydrogenase, quinine 1; Gene ID 18104); Pgd (phosphogluconate dehydrogenase; Gene ID 110208); Gstt3 (glutathione S-transferase, theta 3; Gene ID 103140); Gclc (glutamate-cysteine ligase, catalytic subunit; Gene ID 14629); Oplah (5-oxoprolinase (ATP-hydrolysing); Gene ID 75475); Srxn1 (sulfiredoxin 1 homolog (S. cerevisiae); Gene ID 76650); Cth (cystathionase (cystathionine gamma-lyase); Gene ID 107869); Rnf7 (ring finger protein 7; Gene ID 19823); Car 3 (carbonic anhydrase 3; Gene ID 12350); Epas 1 (endothelial PAS domain protein 1; Gene ID 13819); Glo 1 (glyoxalase1; Gene ID 109801); Rrm2b (ribonucleotide reductase M2 B (TP53 inducible); Gene ID 382985); Tkt (transketolase; Gene ID 21881); Gss (glutathione synthetase; Gene ID 14854); Hif1a (hypoxia inducible factor 1, alpha subunit; Gene ID 15251); Hmox 1 (heme oxygenase (decycling) 1; Gene ID 15368); Sin3a (transcriptional regulator, SIN3A (yeast); Gene ID 20466); Gpx4 (glutathione peroxidase 4; Gene ID 625249); Ggt6 (gamma-glutamyltransferase 6; Gene ID 71522); and Cln8 (ceroid-lipofuscinosis, neuronal 8; Gene ID 26889).

As used herein, the term "cellular stress response" refers to a physiological response in a biological sample (e.g., a cell) to a stressful stimulus, e.g., toxins (e.g., chemotherapeutic agents, heavy metals, toxic chemicals, etc.), irradiation, extreme heat or cold, hypoxia, mechanical stress, shortage of nutrients, and endoplasmic reticulum (ER) stress. In some embodiments, the cellular stress response comprises inducing expression of a cellular stress gene other than an oxidative stress-responsive gene as described herein. As used herein, cellular stress genes include, but are not limited to, ER stress-responsive genes (genes that are induced in response to ER stress), genotoxic stress-responsive genes (genes that are induced in response to genotoxic stress), heat stress-responsive genes (genes that are induced in response to heat stress), and cold stress-responsive genes (genes that are induced in response to cold stress). Exemplary cellular stress genes other than oxidative-stress responsive genes include, but are not limited to, growth arrest and DNA-damage-inducible, alpha (Gadd45a); activating transcription factor 4 (Atf4); heatshock 70 kDa protein 6 (Hspa6); cyclin-dependent kinase inhibitor 1A (Cdkn1a); heatshock protein 60 (Hsp60); heatshock protein 70 (Hsp70); heatshock protein 90 (Hsp90); heatshock protein 100 (Hsp100); 78 kDa glucose-related protein (Grp78); Bcl2-associated protein (Bax); and transformed mouse 3T3 cell double minute 2 (Mdm2).

As used herein, the terms "induce expression," "inducing expression," or "induction of expression" refer to increasing expression of a nucleic acid or protein (e.g., an oxidative stress-responsive gene) in a biological sample of interest (e.g., a cell or tissue exhibiting oxidative stress) at a detectably greater level in comparison to a control biological sample. In some embodiments, the control biological sample is a sample in which oxidative stress and/or cellular stress has not been induced. The term includes increased expression in a biological sample of interest due to transcription, post transcriptional processing, translation, post-translational processing, cellular localization (e.g, organelle, cytoplasm, nucleus, cell surface), and RNA and protein stability, as compared to a control biological sample. Induction of expression can be 10%, 15%, 20%, 25%, 30%, 40%, 50%, 60%, 70%, 80%, 90% or more in comparison to a control biological sample. In some embodiments, induction of expression is 1-fold, 2-fold, 3-fold, 4, 5, 6, 7, 8, 9, 10, or 15-fold or more higher levels of transcription or translation in comparison to a control biological sample. Induction of expression can be detected using conventional techniques for detecting mRNA (e.g., RT-PCR, PCR, hybridization) or proteins (e.g., ELISA, immunohistochemical techniques, mass spectroscopy, Luminex® xMAP technology).

As used herein, the terms "does not significantly induce expression" or "does not significantly activate" refer to an increase in expression of a nucleic acid or protein that does not exceed a threshold level. In some embodiments, a compound does not significantly induce expression of a nucleic acid or protein when the increase in levels of transcription or translation for a biological sample of interest (e.g., one that has been contacted with a test compound) is less than 50%, less than 40%, less than 30%, less than 25% or less as compared to a baseline (e.g., the biological sample prior to being contacted with the test compound) or a control biological sample (e.g., one that has not been contacted with a test compound). In some embodiments, a compound does not significantly induce expression of a nucleic acid or protein when the increase in levels of transcription or translation for a biological sample of interest (e.g., one that has been contacted with a test compound) does not exceed the level of transcription or translation with a known positive control. One of skill in the art will recognize that for determining whether there is significant expression, induction, activation, production, etc. of a biological marker as described herein, the threshold that is used can vary based on the type of assay used and the sensitivity of the assay.

With respect to measuring activation of NF-κB by measuring nuclear translocation of NF-κB protein, the term "does not significantly activate" refers to a level of nuclear translocation of NF-κB protein in a biological sample of interest that does not exceed the level of nuclear translocation of NF-κB protein by a known positive control, or that is less than a 25%, less than 20%, less than 15% or less increase over a baseline level or negative control of nuclear translocation for the sample.

The term "does not significantly increase ROS production" refers to a less than 25%, less than 20%, less than 15% or less increase in levels of one or more reactive oxygen species (ROS) in a biological sample of interest as compared to a baseline level or negative control when measured in a cell by cell assay, or an increase in levels of ROS in a biological sample of interest that does not exceed the increase in ROS levels by a known positive control. In some embodiments, the known positive control is curcumin. In some embodiments, the known positive control is celestrol.

The term "does not significantly decrease the level of glutathione" refers to a less than 25%, less than 20%, less than 15% or less decrease in cellular glutathione in a biological sample of interest as compared to a baseline level or negative control when measured in a luminescence assay, or a decrease in levels of cellular glutathione in a biological sample of interest that does not exceed the decrease in cellular glutathione levels by a known positive control.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions), complementary sequences, splice variants, and nucleic acid sequences encoding truncated forms of proteins, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term nucleic acid is used interchangeably with gene, cDNA, mRNA, oligonucleotide, and polynucleotide.

The terms "identical" or "percent identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.*, 2:482 (1981), by the homology alignment algorithm of Needleman & Wunsch, *J. Mol. Biol.*, 48:443 (1970), by the search for similarity method of Pearson & Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA*, 89:10915 (1989)) alignments (B) of 50, expectation (E) of 10, M=5, N=−4, and a comparison of both strands.

As used herein, the term "compound" refers to any molecule, either naturally occurring or synthetic, e.g., peptide, protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, peptidomimetic (e.g., the apolipoprotein mimetic peptide L4F), lipid, fatty acid, siRNA, polynucleotide, oligonucleotide, etc., to be tested for the capacity to selectively induce an oxidative stress response. The compound to be tested can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "screening hit") with some desirable property or activity, e.g., inhibiting activity, creating variants of the screening hit, and evaluating the property and activity of those variants. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

As used herein, an "analog" refers to a compound that is a structural derivative of a parent compound, in which one or more atoms or functional groups is different from the parent compound. An analog may have superior stability, solubility, efficacy, half-life, and the like as compared to the parent compound.

A "biological sample" includes sections of tissues such as biopsy and autopsy samples, and frozen sections taken for histologic purposes. Such samples include blood and blood fractions or products (e.g., serum, plasma, platelets, red blood cells, and the like); sputum or saliva; kidney, lung, liver, heart, brain, nervous tissue, thyroid, eye, skeletal muscle, cartilage, or bone tissue; cultured cells, e.g., primary cultures, explants, and transformed cells, stem cells, stool, urine, etc. A biological sample is typically obtained from a "subject," i.e., a eukaryotic organism, most preferably a mammal such as a primate, e.g., chimpanzee or human; cow; dog; cat; a rodent, e.g., guinea pig, rat, or mouse; rabbit; or a bird; reptile; or fish.

As used herein, the phrase "disease associated with oxidative stress" refers to a disease state which is marked by an imbalance between the production of reactive oxygen species (ROS) and the basal regulation of ROS. For example, diseases associated with oxidative stress include, but are not limited to, fibrotic diseases (e.g., fibrotic diseases of the lung such as COPD, idiopathic pulmonary fibrosis, and sarcoidosis; fibrotic diseases of the liver including those caused by alcoholic cirrhosis, steatosis, cholestasis, drug side effect, and viral infection; and fibrotic diseases of the skin including autoimmune diseases such as scleroderma), neurodegenerative diseases, cardiovascular diseases and conditions related to the effects of cardiovascular disease (e.g., effects of hypertension such as nephropathy, congestive heart failure, and stroke), renal diseases, inflammatory diseases, liver diseases, eye diseases, thyroid diseases, lung diseases, skin diseases, gastrointestinal diseases (e.g., Crohn's disease, irritable bowel syndrome, and celiac disease), viral infections, osteoporosis, and diabetes. In some embodiments, the diseases that may be treated with a compound that selectively induces an oxidative stress response as described herein include, but are not limited to, sickle cell anemia, thalassemia, Parkinson's disease, amyotrophic lateral sclerosis, Charcot-Marie-Tooth syndrome, Friedreich's ataxia, Ataxia-Telangiectasia, Down Syndrome, Fanconi Anaemia, and Werner syndrome.

As used herein, the terms "administer," "administered," or "administering" refer to methods of introducing to a subject the compounds of the present invention. The term is not limited to any specific mode of delivery, and can include, for example, topical delivery, parenteral delivery, intravenous delivery, intradermal delivery, intramuscular delivery, colonical delivery, rectal delivery or intraperitoneal delivery. The compounds of the present invention can also be administered as part of a composition or formulation.

As used herein, the term "non-naturally occurring organic molecule" refers to an organic molecule that does not occur in nature, for example, a compound that is synthesized in a laboratory with the direct or indirect aid of a human. In some embodiments, the non-naturally-occurring organic molecule is also a small organic molecule, as defined above.

As used herein, the term "selective heme oxygenase 1 inducer" refers to a compound that induces an oxidative stress response in a cell but does not significantly activate a cellular stress response in the cell. In addition, the phrase "selectively inducing an oxidative stress response in a cell" refers to inducing an oxidative stress response in a cell without significantly activating a cellular stress response in the cell.

Embodiments of the Invention

II. Introduction

In response to elevated reactive oxygen species (ROS) levels, cells induce expression of oxidative stress-responsive genes, such as genes encoding proteins that degrade ROS or increase levels of the cell's endogenous antioxidant molecules. One such gene is HMOX1. Induction of expression of HMOX1 and other oxidative stress-responsive genes is regulated in part by the transcription factor Nrf2. Without being bound to a particular theory, it is believed that in the absence of oxidative stress, the adaptor protein Keap1 forms a heterodimer with Nrf2, targeting Nrf2 for proteolysis and suppressing Nrf2-mediated transcription. Upon exposure of cells to chemical electrophiles or agents that elevate ROS, the interaction of Keap1 with Nrf2 is weakened and Nrf2 levels in the cell increase, which in turn increases Nrf2 levels in the nucleus and leads to induction of oxidative stress-responsive genes. Nrf2 activity is also regulated by the transcriptional repressor Bach1, which occludes binding of Nrf2 to the promoter region of oxidative stress-responsive genes.

In order to mitigate the effects of oxidative stress in a cell, e.g., in disease settings, it is therefore desirable to identify compounds that promote the induction of expression of oxidative stress-responsive genes, for example, compounds that modulate the interaction of Nrf2 with Keap1 or Bach1 to increase Nrf2 activity. However, it is also desirable that such compounds not act as electrophiles or otherwise incite a stress response in the cell.

Accordingly, the present invention relates to methods of identifying compounds that respond to oxidative stress in a biological sample by selectively inducing expression of an oxidative stress-responsive gene while not significantly inducing activation of other cellular stress pathways in the sample. Compounds identified by the methods of the present invention will exhibit a biological profile of being able to induce expression of an oxidative stress-responsive gene (e.g., one or more of the genes listed in Table 1 below), while not significantly inducing expression of cellular stress genes other than oxidative stress-responsive genes (e.g., ER stress-responsive genes, genotoxic stress-responsive genes, heat stress-responsive genes, and/or cold stress-responsive genes as described herein). In some embodiments, the biological profile of an identified compound further relates to the ability of the compound to activate NF-κB, elevate ROS production, deplete levels of cellular glutathione, and/or activate oxidative stress-responsive genes in cellular genetic backgrounds depleted for Keap1, Nrf2, or Bach1.

The compounds identified by the methods of the present invention, or chemically synthesized analogs of said compounds, may be optimized to have improved biological and/or pharmacological properties. In some embodiments, the identified compounds or chemically synthesized analogs of said compounds are optimized to have improved potency for oxidative stress-responsive gene induction, improved in vivo activity, improved oral bioavailability, extended functional half-life, and/or improved metabolic profile.

In another aspect of the invention, the compounds identified by the methods of the present invention, or the optimized compounds or analogs as described herein, may be useful for treating diseases or conditions associated with oxidative stress.

III. Methods of Identifying Compounds

The present invention provides methods of identifying compounds that decrease oxidative stress by selectively inducing an oxidative stress response in a biological sample. As used herein, "selectively inducing an oxidative stress response" refers to inducing expression of an oxidative stress-responsive gene that is activated by the transcription factor Nrf2, while not significantly inducing expression of a cellular stress gene other than an oxidative stress-responsive gene, e.g., an ER stress-responsive gene, a genotoxic stress-responsive gene, a heat stress-responsive gene, and/or a cold stress-responsive gene.

A. General Methods and Compounds

Using the assays described herein, one can identify lead compounds that are suitable for further testing to identify those that are therapeutically effective in selectively inducing oxidative stress by screening a variety of compounds and mixtures of compounds for a biological activity profile that correlates with selective induction of an oxidative stress response. Compounds of interest can be either synthetic or naturally-occurring.

Screening assays can be carried out in vitro, such as by using cell-based assays, or in vivo, such as by using animal models. The screening methods are designed to screen large chemical or polymer libraries comprising, e.g., small organic molecules, peptides, peptidomimetics, peptoids, proteins, polypeptides, glycoproteins, oligosaccharides, or polynucleotides such as inhibitory RNA (e.g., siRNA, antisense RNA), by automating the assay steps and providing compounds from any convenient source to the assays, which are typically run in parallel (e.g., in microtiter formats on microtiter plates in robotic assays).

The present invention also provides in vitro assays in a high-throughput format. For each of the assay formats described, negative control reactions, in which no compound is provided, and/or positive control reactions, using a known inducer of oxidative stress-responsive genes, can be used. In the high-throughput assays of the present invention, it is possible to screen up to several thousand different compounds in a single day. Each well of a microtiter plate can be used to run a separate assay against a selected potential compound, or, if concentration or incubation time effects are to be observed, every 5-10 wells can test a single compound. Thus, a single standard microtiter plate can assay about 100 (96) compounds. If 1536 well plates are used, then a single plate can easily assay from about 100 to about 1500 different compounds. It is possible to assay many different plates per day; assay screens for up to about 6000-20,000, and even up to about 100,000-1,000,000 different compounds is possible using the integrated systems of the present invention. The steps of labeling, addition of reagents, fluid changes, and detection are compatible with full automation, for instance, using programmable robotic systems or "integrated systems" commercially available, for example, through BioTX Automation (Conroe, Tex.), Qiagen (Valencia, Calif.), Beckman Coulter (Fullerton, Calif.), and Caliper Life Sciences (Hopkinton, Mass.).

Essentially any chemical compound can be tested for its ability to selectively induce an oxidative stress response in a biological sample. Preferred compounds are generally compounds that can be dissolved in aqueous or organic solutions. It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland), as well as providers of small organic molecule and peptide libraries ready for screening, including Chembridge Corp. (San Diego, Calif.), Discovery Partners International (San Diego, Calif.), Triad Therapeutics (San Diego, Calif.), Nanosyn (Menlo Park, Calif.), Affymax (Palo Alto, Calif.), ComGenex (South San Francisco, Calif.), and Tripos, Inc. (St. Louis, Mo.).

In some embodiments, compounds that selectively induce an oxidative stress response can be identified by screening a combinatorial library containing a large number of potential therapeutic compounds (potential oxidative stress-responsive gene-inducing compounds). Such "combinatorial chemical or peptide libraries" can be screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

The preparation and screening of combinatorial chemical libraries is well known to those of skill in the art (see, e.g., Beeler et al., *Curr Opin Chem Biol.*, 9:277 (2005); and Shang et al., *Curr Opin Chem Biol.*, 9:248 (2005)). Libraries of use in the present invention can be composed of amino acid compounds, nucleic acid compounds, carbohydrates, or small organic compounds. Carbohydrate libraries have been described in, for example, Liang et al., *Science*, 274:1520-1522 (1996); and U.S. Pat. No. 5,593,853.

Representative amino acid compound libraries include, but are not limited to, peptide libraries (see, e.g., U.S. Pat. Nos. 5,010,175; 6,828,422; and 6,844,161; Furka, *Int. J. Pept. Prot. Res.*, 37:487-493 (1991); Houghton et al., *Nature*, 354:84-88 (1991); and Eichler, *Comb Chem High Throughput Screen.*, 8:135 (2005)), peptoids (PCT Publication No. WO 91/19735), encoded peptides (PCT Publication No. WO 93/20242), random bio-oligomers (PCT Publication No. WO 92/00091), vinylogous polypeptides (Hagihara et al., *J. Amer. Chem. Soc.*, 114:6568 (1992)), nonpeptidal peptidomimetics with β-D-glucose scaffolding (Hirschmann et al., *J. Amer. Chem. Soc.*, 114:9217-9218 (1992)), peptide nucleic acid libraries (see, e.g., U.S. Pat. No. 5,539,083), antibody libraries (see, e.g., U.S. Pat. Nos. 6,635,424 and 6,555,310; PCT Application No. PCT/US96/10287; and Vaughn et al., *Nature Biotechnology*, 14:309-314 (1996)), and peptidyl phosphonates (Campbell et al., *J. Org. Chem.*, 59:658 (1994)).

Representative nucleic acid compound libraries include, but are not limited to, genomic DNA, cDNA, mRNA, inhibitory RNA (e.g., RNAi, siRNA), and antisense RNA libraries. See, e.g., Ausubel, *Current Protocols in Molecular Biology*, eds. 1987-2005, Wiley Interscience; and Sambrook and Russell, *Molecular Cloning: A Laboratory Manual*, 2000, Cold Spring Harbor Laboratory Press. Nucleic acid libraries are described in, for example, U.S. Pat. Nos. 6,706,477; 6,582,914; and 6,573,098. cDNA libraries are described in, for example, U.S. Pat. Nos. 6,846,655; 6,841,347; 6,828,098; 6,808,906; 6,623,965; and 6,509,175. RNA libraries, for example, ribozyme, RNA interference, or siRNA libraries, are described in, for example, Downward, *Cell*, 121:813 (2005) and Akashi et al., *Nat. Rev. Mol. Cell Biol.*, 6:413 (2005). Antisense RNA libraries are described in, for example, U.S. Pat. Nos. 6,586,180 and 6,518,017.

Representative small organic molecule libraries include, but are not limited to, diversomers such as hydantoins, benzodiazepines, and dipeptides (Hobbs et al., *Proc. Nat. Acad. Sci. USA*, 90:6909-6913 (1993)); analogous organic syntheses of small compound libraries (Chen et al., *J. Amer. Chem. Soc.*, 116:2661 (1994)); oligocarbamates (Cho et al., *Science*, 261:1303 (1993)); benzodiazepines (e.g., U.S. Pat. No. 5,288,514; and Baum, *C&EN*, January 18, page 33 (1993)); isoprenoids (e.g., U.S. Pat. No. 5,569,588); thiazolidinones and metathiazanones (e.g., U.S. Pat. No. 5,549,974); pyrrolidines (e.g., U.S. Pat. Nos. 5,525,735 and 5,519,134); morpholino compounds (e.g., U.S. Pat. No. 5,506,337); tetracyclic benzimidazoles (e.g., U.S. Pat. No. 6,515,122); dihydrobenzpyrans (e.g., U.S. Pat. No. 6,790,965); amines (e.g., U.S. Pat. No. 6,750,344); phenyl compounds (e.g., U.S. Pat. No. 6,740,712); azoles (e.g., U.S. Pat. No. 6,683,191); pyridine carboxamides or sulfonamides (e.g., U.S. Pat. No. 6,677,452); 2-aminobenzoxazoles (e.g., U.S. Pat. No. 6,660,858); isoindoles, isooxyindoles, or isooxyquinolines (e.g., U.S. Pat. No. 6,667,406); oxazolidinones (e.g., U.S. Pat. No. 6,562,844); and hydroxylamines (e.g., U.S. Pat. No. 6,541,276).

Devices for the preparation of combinatorial libraries are commercially available. See, e.g., 357 MPS and 390 MPS from Advanced Chem. Tech (Louisville, Ky.), Symphony from Rainin Instruments (Woburn, Mass.), 433A from Applied Biosystems (Foster City, Calif.), and 9050 Plus from Millipore (Bedford, Mass.).

B. Biological Activity Profile

The biological activity profile for identifying compounds that decrease oxidative stress in a biological sample comprises the criteria of oxidative stress-responsive gene induction and lack of cellular stress gene induction. In some embodiments, the biological activity profile further comprises the criteria of lack of NF-κB activation; lack of increased reactive oxygen species (ROS) production; lack of glutathione depletion; oxidative stress-responsive gene induction that is dependent on Nrf2; oxidative stress-responsive gene induction that is independent of Keap1; and/or oxidative stress-responsive gene induction that is dependent on Bach1.

Oxidative Stress-Responsive Genes

In some embodiments, a selected-for compound induces expression in a biological sample of an oxidative stress-responsive gene that is responsive to transcription factor Nrf2. As used herein, an oxidative stress-responsive gene is "responsive to transcription factor Nrf2" if transcription of the gene is activated (directly or indirectly) by Nrf2. Non-limiting examples of an oxidative stress-responsive gene that is responsive to transcription factor Nrf2 are listed in Table 1 below.

TABLE 1

Oxidative stress-responsive genes

| Gene name | Gene symbol | Entrez Gene ID |
|---|---|---|
| proteasome (prosome, macropain) subunit, beta type 5 | Psmb5 | 19173 |
| ATX1 (antioxidant protein 1) homolog 1 (yeast) | Atox1 | 11927 |
| glutathione S-transferase, mu 1 | Gstm1 | 14862 |
| demethyl-Q 7 | Coq7 | 12850 |
| amyotrophic lateral sclerosis 2 (juvenile) homolog (human) | Als2 | 74018 |
| glutathione S-transferase, alpha 1 | Gsta1 | 14857 |
| glutathione S-transferase, alpha 2 | Gsta2 | 14858 |
| Janus kinase 2 | Jak2 | 16452 |
| thioredoxin reductase 1 | Txnrd1 | 50493 |
| glutathione reductase | Gsr | 14782 |
| NAD(P)H dehydrogenase, quinone 1 | Nqo1 | 18104 |
| phosphogluconate dehydrogenase | Pgd | 110208 |
| glutathione S-transferase, theta 3 | Gstt3 | 103140 |
| glutamate-cysteine ligase, catalytic subunit | Gclc | 14629 |
| 5-oxoprolinase (ATP-hydrolysing) | Oplah | 75475 |
| sulfiredoxin 1 homolog (*S. cerevisiae*) | Srxn1 | 76650 |
| cystathionase (cystathionine gamma-lyase) | Cth | 107869 |
| ring finger protein 7 | Rnf7 | 19823 |
| carbonic anhydrase 3 | Car3 | 12350 |
| endothelial PAS domain protein 1 | Epas1 | 13819 |
| glyoxalase 1 | Glo1 | 109801 |
| ribonucleotide reductase M2 B (TP53 inducible) | Rrm2b | 382985 |

TABLE 1-continued

Oxidative stress-responsive genes

| Gene name | Gene symbol | Entrez Gene ID |
|---|---|---|
| transketolase | Tkt | 21881 |
| glutathione synthetase | Gss | 14854 |
| hypoxia inducible factor 1, alpha subunit | Hif1a | 15251 |
| heme oxygenase (decycling) 1 | Hmox1 | 15368 |
| transcriptional regulator, SIN3A (yeast) | Sin3a | 20466 |
| glutathione peroxidase 4 | Gpx4 | 625249 |
| gamma-glutamyltransferase 6 | Ggt6 | 71522 |
| ceroid-lipofuscinosis, neuronal 8 | Cln8 | 26889 |

In some embodiments, the oxidative stress-responsive gene is selected from the group consisting of heme oxygenase 1 (HMOX1), NAD(P)H:quinine oxidoreductase (NQO1), thioredoxin reductase 1 (TXNRD1), glutamylcysteine ligase catalytic subunit (GCLC), and GSH S-transferase (GST). In some embodiments, the oxidative stress-responsive gene is HMOX1.

In some embodiments, the methods of the present invention comprise determining whether a compound induces expression of one, two, three, or more oxidative stress-responsive genes as described herein. In some embodiments, the methods of the present invention comprise determining whether a compound induces expression of HMOX1 and at least one more oxidative stress-responsive gene.

A compound induces expression of an oxidative stress-responsive gene if a biological sample that is contacted with the compound exhibits increased expression of an oxidative stress-responsive gene relative to a control biological sample (e.g., a biological sample that has not been contacted with the compound). In some embodiments, a compound is identified as inducing expression of an oxidative stress-responsive gene if the increase in expression is at least about one-fold as compared to a control sample. In some embodiments, a compound is identified as inducing expression of an oxidative stress-responsive gene if the increase in expression is at least about two-fold as compared to a control sample. In some embodiments, a compound is identified as inducing expression of an oxidative stress-responsive gene if the increase in expression is at least about three-fold, at least about four-fold, five-fold, seven-fold, ten-fold, or more as compared to a control sample.

In some embodiments, the induction of expression of an oxidative stress-responsive gene in a biological sample by a compound is compared to the induction of expression of the oxidative stress-responsive gene in the biological sample by a known inducer of oxidative stress-responsive genes, e.g., Cobalt protoporphyrin IX (CoPP). The EC50, or the effective concentration of a compound that is required to induce a response halfway between the baseline and the maximum response, can be determined for the compound of interest and compared to the EC50 for a known inducer of oxidative stress-responsive genes such as CoPP. In some embodiments, a selected-for compound will be one that induces expression of an oxidative stress-responsive gene with an EC50 that is less than or equal to that of a known inducer of the oxidative stress-responsive gene, e.g., CoPP.

Cellular Stress Genes

In some embodiments, a selected-for compound does not significantly induce expression in a biological sample of a cellular stress gene other than an oxidative stress-responsive gene. As used herein, "cellular stress gene other than an oxidative stress-responsive gene" refers to an ER stress-responsive gene, a genotoxic stress-responsive gene, a heat stress-responsive gene, and/or a cold stress-responsive gene. Non-limiting examples of a cellular stress gene other than an oxidative stress-responsive gene are listed in Table 2 below.

TABLE 2

Cellular stress genes

| Gene name | Gene symbol | Entrez Gene ID |
|---|---|---|
| Growth arrest and DNA-damage-inducible, alpha | Gadd45a | 1647 |
| Activating transcription factor 4 | Atf4 | 468 |
| Heatshock 70 kDa protein 6 | Hspa6 | 3310 |
| Cyclin-dependent kinase inhibitor 1A | Cdkn1a | 5063 |
| Transformed mouse 3T3 cell double minute 2 | Mdm2 | 4193 |
| Heatshock protein 60 | Hsp60 | 3329 |
| Heatshock protein 70 | Hsp70 | 3308 |
| Heatshock protein 90 | Hsp90 | 3320 |
| Heatshock protein 100 | Hsp100 | 7184 |
| 78 kDa glucose-regulated protein | Grp78 | 3309 |
| Bcl2-associated protein | Bax | 581 |

In some embodiments, the methods of the present invention comprise determining whether a compound induces expression of one, two, three, or more cellular stress genes as described herein. A compound does not significantly induce expression of a cellular stress gene in a biological sample if it exhibits an increase in expression of the cellular stress gene that is less than 50%, less than 40%, less than 30%, less than 25% or less as compared to a baseline or a negative control, or if it exhibits an increase in expression of the cellular stress gene that does not exceed the level of expression of the cellular stress gene for a known control. In some embodiments, the control is Cobalt protoporphyrin IX (CoPP).

NF-κB Activation

In some embodiments, a selected-for compound does not significantly activate the transcription factor nuclear factor-kappaB (NF-κB) in a biological sample. NF-κB activation in a biological sample can be measured by determining the level of gene or protein expression of a NF-κB-regulated gene, and/or by assaying for cytoplasm to nucleus translocation of activated NF-κB. NF-κB-regulated genes that can be measured according to the methods of the present invention include, but are not limited to, adhesion molecules (e.g., ICAM-1 (intercellular adhesion molecule; Entrez Gene ID 3383) and VCAM-1 (vascular cell adhesion molecule; Entrez Gene ID 7412)), enzymes (e.g., iNOS (inducible nitric oxide synthase; Entrez Gene ID 4843)), cytokines (e.g., IL-6 (interleukin 6; Entrez Gene ID 3569), IL-12 (interleukin 12 alpha, Entrez Gene ID 3592; or interleukin 12 beta, Entrez Gene ID 3593), IL-1α (interleukin 1 alpha; Entrez Gene ID 3552), and IL-1β (interleukin 1 beta; Entrez Gene ID 3553)), and chemokines (e.g., IL-8 (interleukin 8; Entrez Gene ID 3576)). In some embodiments, activation of NF-κB is determined by measuring the induction of expression of a NF-κB-regulated gene selected from the group consisting of ICAM-1, iNOS, VCAM-1, IL-6, and IL-1β.

A compound does not significantly activate NF-κB in a biological sample if it exhibits an increase in expression of the NF-κB-regulated gene that is less than 50%, less than 40%, less than 30%, less than 25% or less as compared to a baseline or a negative control, or if it exhibits an increase in expression of the NF-κB-regulated gene that does not exceed the level of expression of the NF-κB-regulated gene for a known positive control. Alternatively or additionally, a compound does not significantly activate NF-κB in a biological sample if it exhibits a level of nuclear translocation of NF-κB protein in a biological sample of interest that does not exceed the level of nuclear translocation of NF-κB protein by a known positive control, or that is less than a 25%, less than 20%, less than 15% or less increase over a baseline level or negative control of nuclear translocation for the sample.

Cellular Redox Status

In some embodiments, a selected-for compound does not significantly increase reactive oxygen species (ROS) production in a biological sample. ROS that can be measured according to the methods of the present invention include, but are not limited to, hydrogen peroxide ($H_2O_2$), hydroxyl anion ($.OH^-$), nitric oxide ($NO^-$), hydroperoxyl radical ($.OOH$), peroxynitrite ($OONO^-$), and superoxide anion ($.O_2^-$). A compound does not significantly increase ROS production in a biological sample if it exhibits a less than 25%, less than 20%, less than 15% or less increase in ROS production as compared to a baseline or a negative control when measured in a cell by cell assay, or if it exhibits an increase in ROS production that does not exceed the level of ROS production for a known positive control (e.g., curcumin or celestrol).

In some embodiments, a selected-for compound does not significantly decrease the level of glutathione in a biological sample. As used herein, "glutathione" refers to reduced glutathione ("GSH") as well as oxidized glutathione ("GSSG"). A compound does not significantly decrease the level of glutathione in a biological sample if it exhibits a less than 25%, less than 20%, less than 15% or less decrease in cellular glutathione levels as compared to a baseline level or negative control when measured in a luminescence assay, or if it exhibits a decrease in cellular glutathione levels that does not exceed the decrease in cellular glutathione levels by a known positive control.

Cellular Genetic Backgrounds

In some embodiments, the biological activity profile for a screened compound is measured in a biological sample having a genetic background other than a wild-type (i.e., naturally occurring) genetic background, e.g., a genetic background that has decreased levels of, or is depleted of, the transcription factor Nrf2, the transcriptional repressor Bach1, and/or the adaptor protein Keap1.

In some embodiments, the biological activity profile for the screened compound comprises oxidative stress-responsive gene induction that is dependent on Nrf2, and accordingly, a selected-for compound is a compound that does not significantly increase expression of an oxidative stress-responsive gene in a biological sample with decreased or depleted Nrf2 relative to a control biological sample (e.g., a biological sample with decreased or depleted Nrf2 that has not been contacted with the compound). In some embodiments, the biological activity profile for the screened compound comprises oxidative stress-responsive gene induction that is dependent on Bach1, and accordingly, a selected-for compound is a compound that does not significantly increase expression of an oxidative stress-responsive gene in a biological sample with decreased or depleted Bach1 relative to a control biological sample (e.g., a biological sample with decreased or depleted Bach1 that has not been contacted with the compound).

In some embodiments, the biological activity profile for the screened compound comprises oxidative stress-responsive gene induction that is independent of Keap1, and accordingly, a selected-for compound is a compound that increases expression of an oxidative stress-responsive gene in a biological sample with decreased or depleted Keap1 relative to a control biological sample (e.g., a biological sample with decreased or depleted Keap1 that has not been contacted with the compound).

The genetic background of a biological sample (e.g., a cell or tissue) may be altered according to any known method, including but not limited to inhibitory nucleic acids and the generation of transgenic or knockout animals (e.g., mice), from which a biological sample having a modified genetic background can be obtained. Inhibitory nucleic acids to Nrf2, Bach1, and/or Keap1, such as siRNA, shRNA, ribozymes, or antisense molecules, can be synthesized and introduced into cells using methods known in the art in order to decrease the level of Nrf2, Bach1, and/or Keap1 in those cells. Molecules can be synthesized chemically or enzymatically in vitro (Micura, *Agnes Chem. Int. Ed. Emgl.* 41: 2265-9 (2002); Paddison et al., *Proc. Natl. Acad. Sci. USA*, 99: 1443-8 2002) or endogenously expressed inside the cells in the form of shRNAs (Yu et al., *Proc. Natl. Acad. Sci. USA*, 99: 6047-52 (2002); McManus et al., *RNA* 8, 842-50 (2002)). Plasmid-based expression systems using RNA polymerase III U6 or H1, or RNA polymerase II U1, small nuclear RNA promoters, have been used for endogenous expression of shRNAs (Brummelkamp et al., *Science*, 296: 550-3 (2002); Sui et al., *Proc. Natl. Acad. Sci. USA*, 99: 5515-20 (2002); Novarino et al., *J. Neurosci.*, 24: 5322-30 (2004)). Synthetic siRNAs can be delivered by electroporation or by using lipophilic agents (McManus et al., *RNA* 8, 842-50 (2002); Kishida et al., *J. Gene Med.*, 6: 105-10 (2004)). Alternatively, plasmid systems can be used to stably express small hairpin RNAs for the suppression of target genes (Dykxhoorn et al., *Nat. Rev. Mol. Biol.*, 4: 457-67 (2003)). Various viral delivery systems have been developed to deliver shRNA-expressing cassettes into cells that are difficult to transfect (Brummelkamp et al., *Cancer Cell*, 2: 243-7 (2002); Rubinson et al., *Nat. Genet.*, 33: 401-6 2003). Furthermore, siRNAs can also be delivered into live animals. (Hasuwa et al., *FEBS Lett.*, 532, 227-30 (2002); Carmell et al., *Nat. Struct. Biol.*, 10: 91-2 (2003); Kobayashi et al., *J. Pharmacol. Exp. Ther.*, 308: 688-93 (2004)).

Ribozymes that cleave mRNA at site-specific recognition sequences can be used to destroy target mRNAs, particularly through the use of hammerhead ribozymes. Hammerhead ribozymes cleave mRNAs at locations dictated by flanking regions that form complementary base pairs with the target mRNA. The construction and production of hammerhead ribozymes is well known in the art.

Methods of generating transgenic, knockout, and conditional knockout animals are well known in the art for a number of species and involve routine techniques in the field of recombinant genetics. See, e.g., Sambrook & Russell, *Molecular Cloning, A Laboratory Manual* (3rd Ed, 2001); Kriegler, *Gene Transfer and Expression: A Laboratory Manual* (1990); *Current Protocols in Molecular Biology* (Ausubel et al., eds., 1994-1999). Methods for generating mice lacking Nrf2, Keap1, and/or Bach1, either throughout the entire genome or in a cell-specific manner, have been previously described. See, e.g., Taguchi et al., Mol. Cell Biol. 30:3016-3026 (2010); Zhang et al., Toxicol. Appl. Pharmacol. 245:326-334 (2010); Sakoda et al., Neurosci. Lett. 440:160-165 (2008); Sun et al., EMBO J. 21:5216-5224 (2002). From these transgenic, knockout, and conditional knockout animals, primary cells having the genetic background of interest can be harvested and subcultured using cell culture methods that are known in the art.

C. Assays for Measuring Biological Activity

In some embodiments, the biological activity profile for a compound is determined by measuring induction of mRNA or protein expression or activity in a biological sample of interest, or by measuring production or depletion of a molecule (e.g., ROS or glutathione) in a biological sample of interest. In some embodiments, the expression of more than one gene (e.g., an oxidative stress-responsive gene, a cellular stress gene, and/or an NF-κB-regulated gene) is measured using a multiplex assay.

Measuring induction of mRNA or protein expression or activity involves determining the level of polynucleotide or polypeptide expression or activity in a biological sample that has been contacted with the compound and comparing the level to a baseline or range. Typically, the baseline value is representative of the expression or activity of the polynucleotide or polypeptide in a biological sample that has not been contacted with the compound.

Measuring production or depletion of a molecule involves determining the amount or concentration of the molecule (e.g., ROS or glutathione) in a biological sample that has been contacted with the compound and comparing the amount or concentration to a baseline or range. Typically, the baseline value is representative of the amount or concentration of the molecule in a biological sample that has not been contacted with the compound.

1. Measuring Induction of mRNA

Polynucleotide expression can be analyzed using routine techniques such as northern analysis, reverse-transcriptase polymerase chain reaction (RT-PCR), microarray hybridization, sequence analysis, or any other methods based on hybridization to a nucleic acid sequence (e.g., slot blot hybridization). Applicable PCR amplification techniques are described in, e.g., Ausubel et al., Theophilus et al., and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002. In some embodiments, the microarray comprises a direct hybridization assay (Illumina, San Diego, Calif.) for analyzing RNA expression profiles from total RNA, in which total RNA is analyzed by first- and second-strand reverse transcription, followed by an in vitro transcription labeling amplification step, followed by array hybridization, washing, blocking, and label detection.

Non-limiting examples of sequence analysis include Sanger sequencing, capillary array sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis.

In some embodiments, real-time or quantitative PCR is used to measure induction of mRNA in a biological sample. RNA extraction can be performed by any method known to those of skill in the art, e.g., using TRIZOL® and RNEASY®. Real-time PCR can be performed by any method known to those of skill in the art, e.g., TAQMAN® Real-Time PCR using Applied Biosystem assays. Gene expression is calculated relative to control RNA (e.g., RNA from a biological sample that has not been contacted with the compound being screened), and expression is normalized to housekeeping genes. Suitable oligonucleotide primers are selected by those of skill in the art.

A detectable moiety can be used in the assays described herein (direct or indirect detection). A wide variety of detectable moieties can be used, with the choice of label depending on the sensitivity required, ease of conjugation with the probe, stability requirements, and available instrumentation and disposal provisions. Suitable detectable moieties include, but are not limited to, radionuclides, fluorescent dyes (e.g., fluorescein, fluorescein isothiocyanate (FITC), OREGON GREEN™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

2. Measuring Induction of Protein

In another embodiment, antibody reagents can be used in assays to measure induction of protein expression in a biological sample using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used (see, e.g., Self et al., *Curr. Opin. Biotechnol.*, 7:60-65 (1996)). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); immunofluorescence (IF); fluorescence polarization immunoassays (FPIA); and chemiluminescence assays (CL). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)).

Specific immunological binding of the antibody to a protein can be detected directly or indirectly. Direct labels include fluorescent or luminescent tags, metals, dyes, radionuclides, and the like, attached to the antibody. An antibody labeled with iodine-125 ($^{125}I$) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously. In some embodiments, the amount of signal can be quantified using an automated high-content imaging system. High-content imaging systems are commercially available (e.g., IMAGEXPRESS, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different biomarkers. Such formats include protein microarrays, or "protein chips" (see, e.g., Ng et al., J. Cell Mol. Med., 6:329-340 (2002)) and certain capillary devices (see, e.g., U.S. Pat. No. 6,019,944). In these embodiments, each discrete surface location may comprise antibodies to immobilize one or more protein markers for detection at each location. Surfaces may alternatively comprise one or more discrete particles (e.g., microparticles or nanoparticles) immobilized at discrete locations of a surface, where the microparticles comprise antibodies to immobilize one or more protein markers for detection.

The analysis can be carried out in a variety of physical formats. For example, the use of microtiter plates or automation could be used to facilitate the processing of large numbers of test samples.

3. Measuring NF-κB Activation

NF-κB activation in a biological sample can be measured by any known method. In some embodiments, measuring NF-κB activation in a biological sample entails determining the level of nucleic acid or protein expression of a NF-κB-regulated gene. The level of nucleic acid or protein expression of a NF-κB-regulated gene can be measured using any of the methods described above.

In some embodiments, measuring NF-κB activation in a biological sample entails assaying for cytoplasm to nucleus translocation of activated NF-κB. Methods for assaying nuclear translocation of activated NF-κB are known in the art and include, but are not limited to, immunofluorescence assay, electrophoretic mobility shift assay (EMSA), or ELISA or Western blot of nuclear extract. Kits for assaying NF-κB activation are readily commercially available, such as NF-kappaB Activation Assay Kit for ELISA or Western (FIVEphoton Biochemicals, San Diego, Calif.) and NF-κB EMSA Kit (Panomics, Santa Clara, Calif.).

4. Measuring Cellular Redox Status

The production of cellular ROS in a biological sample (e.g., a cell or tissue sample) can be measured by any known assay, including but not limited to chemiluminescence, fluorescent assay, flow cytometry, or electron spin resonance (ESR) spectroscopy. See, e.g., Inoguchi et al., Diabetes 49:1939-1945 (2000) and He et al., Am. J. Physiol. Lung Cell. Mol. Physiol. 289:L916-L924 (2005), each of which is incorporated by reference herein in its entirety. Reagents for the detection of ROS by chemiluminescence or flow cytometry are readily commercially available from Invitrogen (Carlsbad, Calif.). As a non-limiting example, ROS can be detected by incubating a biological sample (e.g., a cell) with a detection reagent such as carboxy-$H_2$DCF-DA (dichlorofluorescein diacetate), a cell-permeant reagent that fluoresces with a characteristic fluorescence spectra upon oxidation within the cell. As a positive control for ROS production, the biological sample can be contacted with a compound that is known to induce ROS production, such as curcumin or celestrol.

Alternatively, ROS production in a biological sample can be measured indirectly, for example by measuring the effect of an agent that acts to restore cellular glutathione levels in a sample (e.g., N-acetyl cysteine ("NAC")) on the test compound's induction of expression of an oxidative stress-responsive gene (e.g., HMOX1). The degree to which NAC can suppress induction of the oxidative stress-responsive gene (e.g., HMOX1) in the presence of the compound of interest is an indicator of the amount of chemical reactivity or ROS stress that the compound is imposing on the cell and thus activating oxidative stress-responsive gene induction. Curcumin and celestrol, which are nearly completely inhibited from inducing HMOX1 expression in the presence of NAC, can be used as positive controls. Oxidative stress-responsive gene induction can be measured using any of the assays described herein for measuring mRNA expression.

The concentration of reduced glutathione in a biological sample (e.g., a cell or tissue sample) can be measured by any known assay, including but not limited to high-performance liquid chromatography (HPLC), capillary electrophoresis, colorimetric assay, bioluminescent assay, or fluorescent assay. See, e.g., Jones, Methods Enzymology 348:93-112 (2002); Camera and Picardo, J. of Chromatography B. 781:181-206 (2002); and Baker et al., Anal. Biochem. 190:360-365 (1990), each of which is incorporated by reference herein in its entirety. Assays for measuring the concentration of glutathione in a sample are commercially available, e.g., GSH-GLO™ (Promega, Madison, Wis.), a luminescence-based assay based on the conversion of a luciferin derivative into luciferin in the presence of glutathione and catalyzed by glutathione S-transferase. Briefly, in the GSH-GLO™ assay, the luminescent signal, which is generated in a coupled reaction with firefly luciferase, is proportional to the amount of glutathione present in the sample.

Signals generated using the assays described herein can be detected as described above, e.g., using a spectrophotometer to detect color from a chromogenic substrate; a luminometer to detect luminescent signal; or a fluorometer to detect fluorescence in the presence of light of a certain wavelength. Assays can be adapted to high-throughput screening applications, e.g., 96- or -384 well plates. If desired, the assays of the present invention can be automated or performed robotically, and the signal from multiple samples can be detected simultaneously. In some embodiments, signal is quantified using an automated high-content imaging system.

D. Biological Samples

Samples for identifying compounds that selectively induce an oxidative stress response may be obtained from any tissue or fluid of a human or non-human animal. In some embodiments, the biological sample is from kidney, lung, liver, heart, brain, nervous tissue, thyroid, eye, skeletal muscle, cartilage, or bone tissue, such as cultured cells, e.g., primary cultures, explants, and transformed cells, derived from a tissue described herein.

In some embodiments, the biological sample comprises a lymphocyte, granulocyte, monocyte, macrophage, mast cell, thrombocyte, erythrocyte, megakaryocyte, dendritic cell, glial cell, pneumocyte, Clara cell, goblet cell, myocardiocyte, pericyte, hepatocyte, Kupffer cell, Paneth cell, osteoblast, osteocyte, chondroblast, chondrocyte, keratinocyte, melanocyte, myocyte, adipocyte, fibroblast, tendon cell, epithelial cell, endothelial cell, smooth muscle cell, skeletal muscle cell, embryonic stem cell, neural stem cell, skin stem cell, mesenchymal stem cell, hematopoietic stem cell, stromal stem cell, or epithelial stem cell.

IV. Optimizing Identified Compounds

In some embodiments, a compound that is identified as having a suitable biological profile is optimized in order to improve the compound's biological and pharmacological properties. To optimize the selected-for compound, structurally related analogs are chemically synthesized to systematically modify the structure of the initially-identified compound.

For chemical synthesis, solid phase synthesis can be used for compounds such as peptides, nucleic acids, organic molecules, etc., since in general solid phase synthesis is a straightforward approach with excellent scalability to commercial scale. Techniques for solid phase synthesis are described in the art. See, e.g., Seneci, *Solid Phase Synthesis and Combinatorial Technologies* (John Wiley & Sons 2002); Barany & Merrifield, *Solid-Phase Peptide Synthesis*, pp. 3-284 in *The Peptides: Analysis, Synthesis, Biology, Vol. 2* (E. Gross and J. Meienhofer, eds., Academic Press 1979).

The synthesized structurally related analogs are screened for potency of induction of oxidative stress-responsive genes according to the screening methods described herein. In some embodiments, a selected-for structurally related analog will be one that induces expression of an oxidative stress-responsive gene with an EC50 that is less than or equal to that of a known inducer of the oxidative stress-responsive gene, e.g., CoPP. In some embodiments, a selected-for structurally related analog further comprises a biological profile of lack of cellular stress gene induction; lack of NF-κB activation; lack of increased reactive oxygen species (ROS) production; and lack of glutathione depletion.

A structurally related analog that is determined to have sufficient potency of induction of an oxidative stress-responsive gene and/or an appropriate biological profile will be further screened for biological and pharmacological properties, including but not limited to oral bioavailability, half-life, metabolism, toxicity, and pharmacodynamic activity (e.g., duration of the therapeutic effect) according to methods known in the art. Typically, the screening of the structurally related analogs is performed in vivo in an appropriate animal model (e.g., a mammal such as a mouse or rat). Animal models for analyzing pharmacological and pharmacokinetic properties, including animal models for various disease states, are well known in the art and are commercially available, e.g., from Charles River Laboratories Int'l, Inc. (Wilmington, Mass.).

In some embodiments, a compound that is identified as having a suitable biological profile, or a structurally related analog thereof, is used for the preparation of a medicament for the treatment of a disease or condition associated with oxidative stress.

V. Methods of Treatment

The invention further provides methods of treating a subject having a disease or a condition associated with oxidative stress using compounds that selectively induce an oxidative stress response as described herein. Compounds suitable for the treatment methods of the present invention are compounds having a biological activity profile comprising the criteria of oxidative stress-responsive gene induction and lack of cellular stress gene induction, and further comprising the criteria of lack of NF-κB activation; lack of increased reactive oxygen species (ROS) production; lack of glutathione depletion ; oxidative stress-responsive gene induction that is dependent on Nrf2; oxidative stress-responsive gene induction that is independent of Keap1; and/or oxidative stress-responsive gene induction that is dependent on Bach1. In order to determine whether a compound has a suitable biological profile for use in treating a subject having a disease associated with oxidative stress, the compound can be screened according to the compound identification methods described herein. In some embodiments, the compound is any of the compounds recited in Table 4 or a structurally related analog thereof, or a pharmaceutically acceptable salt of said compound of structurally related analog. In some embodiments, the compound is any of the compounds recited as Examples in U.S. Patent Application Publication No. 2011/0201604, published Aug. 18, 2011 and incorporated by reference herein in its entirety.

In some embodiments, the method of treating a subject having a disease or condition associated with oxidative stress comprises: identifying the subject having the disease or condition that is associated with oxidative stress; and administering to the subject a therapeutically effective amount of a compound that decreases oxidative stress by selectively inducing an oxidative stress response in the subject, thereby treating the subject having the disease or condition.

A. Methods of Administration and Pharmaceutical Compositions

Compounds that decrease oxidative stress by selectively inducing oxidative stress response, including compounds identified by the methods of the invention and chemically synthesized analogs of said identified compounds, can be administered to a subject according to any known method, such as intravenous administration, e.g., as a bolus or by continuous infusion over a period of time, by intramuscular, intraperitoneal, intracerobrospinal, subcutaneous, intraarticular, intrasynovial, intrathecal, oral, rectal, topical, or inhalation routes. The administration may be local or systemic.

Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra).

Formulations suitable for oral administration can comprise: (a) liquid solutions, such as an effective amount of a compound suspended in diluents, e.g., water, saline, or PEG 400; (b) capsules, sachets, or tablets, each containing a predetermined amount of a compound, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a compound in a flavor, e.g., sucrose, as well as pastilles comprising the compound in an inert base, such as gelatin and glycerin or sucrose and acacia emulsions, gels, and the like containing, in addition to the compound, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component, e.g., a modulator. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of a disease or condition associated with oxidative stress, the compounds utilized in the pharmaceutical methods of the present invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention, should be sufficient to effect a beneficial therapeutic response in the patient over time. The size of the dose will also be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

B. Therapeutic Applications

The methods of the present invention find use in any subject, human or non-human animal (e.g., pig, horse, birds including domestic birds, or other animals, especially those used in animal models such as mouse, rat, ferret, or non-human primate) having a disease or condition associated with oxidative stress. Examples of diseases or conditions associated with oxidative stress include, but are not limited to, fibrotic diseases, neurodegenerative disease, cardiovascular disease, renal disease, inflammatory disease, liver disease, eye disease, thyroid disease, lung disease, skin disease, viral infection, osteoporosis, pregnancy disorders, endometriosis, diabetes, and cancer. As used herein, the term "disease or condition associated with oxidative stress" also includes chronic effects (e.g., tissue damage, chronic inflammation) associated with persistent or long-term increases in oxidative stress due to the diseases or conditions described herein. In some embodiments, the methods of the present invention find use in maintaining an arteriovenous fistula in a subject, reducing ischemic damage in a subject, reducing inflammation associated with transplantation in a subject, or improving graft viability in a graft recipient.

Fibrotic diseases associated with oxidative stress include, but are not limited to, fibrotic diseases of the lung such as COPD, idiopathic pulmonary fibrosis, and sarcoidosis; fibrotic diseases of the liver including those caused by alcoholic cirrhosis, steatosis, cholestasis, drug side effect, and viral infection; and fibrotic diseases of the skin including autoimmune diseases such as scleroderma and psoriasis.

Neurodegenerative diseases associated with oxidative stress include, but are not limited to, Friedreich's ataxia, Alzheimer's disease, Parkinson's disease, amyotrophic lateral sclerosis, multiple sclerosis, cerebral nerve degenerative disease, and Charcot-Marie-Tooth syndrome.

Cardiovascular diseases associated with oxidative stress include, but are not limited to, hypertension, heart failure, hypercholesterolaemia, atherosclerosis, arteriosclerosis, thrombosis, acute coronary thrombosis, deep vein thrombosis, peripheral vascular disease, congestive heart failure, acute coronary syndrome, failure of arterial fistula for dialysis, ischemia reperfusion injury, primary pulmonary hypertension, primary pulmonary arterial hypertension, and secondary pulmonary arterial hypertension.

Renal diseases associated with oxidative stress include, but are not limited to, diabetic nephropathy, glomerular nephritis (glomerulonephritis), and acute tubular necrosis.

Inflammatory diseases associated with oxidative stress include, but are not limited to, asthma, chronic obstructive pulmonary disease, idiopathic pulmonary fibrosis, inflammatory bowel syndrome, Crohn's disease, celiac disease, ulcerative colitis, chronic inflammatory bowel disease, scleroderma, dermatitis, systemic lupus erythematosus, esophagitis, vasculitis, pancreatitis, tendonitis, osteoarthritis, rheumatoid arthritis, ankylosing spondylitis, and chronic inflammation of the brain.

Liver diseases associated with oxidative stress include, but are not limited to, drug induced liver toxicity, nonalcoholic steatohepatitis, and hepatitis, e.g., hepatitis B infection and hepatitis C infection.

Eye diseases and conditions associated with oxidative stress include, but are not limited to, conjunctivitis, glaucoma, uveitis, wound healing (e.g., after surgery such as LASIK), eye trauma, corneal grafts, macular degeneration, cataracts, light retinopathy, diabetic retinopathy, and retinopathy of prematurity, as well as inflammation and tissue damage associated with these diseases.

Thyroid diseases associated with oxidative stress include, but are not limited to, Graves' disease, follicular adenoma, and papillary and follicular carcinomas.

Lung diseases associated with oxidative stress include, but are not limited to, bronchitis, asthma, chronic obstructive pulmonary disease, idiopathic pulmonary fibrosis, pulmonary bronchitis, bronchiectasis, pulmonary edema, and emphysema.

Skin diseases associated with oxidative stress include, but are not limited to, dermatitis, scleroderma, and psoriasis.

Viral infections associated with oxidative stress include both viral replication of viruses, as well as tissue damage (e.g., fibrosis) due to oxidative stress resulting from chronic viral infection, for viruses including but are not limited to human immunodeficiency virus, hepatitis B, hepatitis C, and herpesvirus.

Diabetic conditions include, but are not limited to, type 1 diabetes mellitus, type 2 diabetes mellitus, gestational diabetes, pre-diabetes, hyperglycemia, and metabolic syndrome as well as secondary conditions resulting from diabetic conditions (e.g., congestive heart failure and nephropathy).

In another aspect, the compounds and methods of the present invention can be used to reduce ischemic damage in a subject. In some embodiments, the ischemic damage is associated with cardiac ischemia, brain ischemia, kidney ischemia, ischemial colitis, mesenteric ischemia, or an ischemia-reperfusion injury.

In another aspect, the compounds and methods of the present invention can be used to reduce inflammation associated with transplantation in a subject. In some embodiments, the transplantation is a cell transplantation, a tissue transplantation, or an organ transplantation. Examples of cell transplantation include, but are not limited to, stem cell transplantation (e.g., hematopoietic stem cell transplantation) and islet cell transplantation. Examples of tissue transplantation include, but are not limited to, corneal transplantation, ear transplantation, skin transplantation, heart valve transplantation, bone transplantation, vein transplantation, cartilage transplantation, tendon transplantation, and ligament transplantation. Examples of organ transplantation include, but are not limited to, kidney transplantation, heart transplantation, lung transplantation, liver transplantation, pancreas transplantation, and intestine transplantation.

In another aspect, the compounds and methods of the present invention can be used to improve graft viability in a subject who is a graft recipient. In some embodiments, the graft is a skin graft, a bone graft, a vascular graft (e.g., an artery graft or a vein graft), a nerve graft, a tendon graft, a muscle graft, or a corneal graft.

In another aspect, the compounds and methods of the present invention can be used for maintaining an arteriovenous fistula in a subject. In some embodiments, the arteriovenous fistula is surgically created for hemodialysis treatment.

In some embodiments, a compound of the present invention can be used for the preparation of a medicament for the treatment of any of the diseases or conditions described above (e.g., for a fibrotic disease, neurodegenerative disease, cardiovascular disease, renal disease, inflammatory disease, liver disease, eye disease, thyroid disease, lung disease, skin disease, viral infection, osteoporosis, pregnancy disorder, endometriosis, diabetes, or cancer as described above). In some embodiments, a compound of the present invention can be used for the preparation of a medicament for the reduction of ischemic damage in a subject. In some embodiments, a compound of the present invention can be used for the preparation of a medicament for the reduction of inflammation associated with transplantation in a subject. In some embodiments, a compound of the present invention can be used for the preparation of a medicament for the improvement of graft viability in a subject who is a graft recipient. In some embodiments, a compound of the present invention can be used for the preparation of a medicament for the maintenance of an arteriovenous fistula in a subject.

VI. Compositions, Kits, and Arrays

The invention further provides compositions, kits and integrated systems for practicing the methods described herein.

The invention provides assay compositions for use in solid phase assays; such compositions can include, for example, one or more polynucleotides or polypeptides used to identify compounds that decrease oxidative stress (e.g., polynucleotides or polypeptides of oxidative stress-responsive genes, cellular stress genes, or NF-κB-regulated genes) immobilized on a solid support, and a labeling reagent. In each case, the assay compositions can also include additional reagents that are desirable for hybridization. Appropriate controls for carrying out the screen (e.g., known activators of oxidative stress-responsive genes such as CoPP) can also be included in the assay compositions.

The invention also provides kits for carrying out the screening or treatment methods of the invention. Kits for carrying out the treatment methods of the invention can include the compound that decreases oxidative stress, e.g., in a pharmaceutically acceptable carrier, as well as other components. Kits for carrying out the screening methods of the invention can include chemical reagents for identifying the biological profile of a compound that decreases oxidative stress as well as other components. In addition, the kits of the present invention can include, without limitation, instructions to the kit user (e.g., directions for use of the compound in treating the subject, directions for use of the chemical reagent in identifying a compound that decreases oxidative stress, etc.); apparatus and/or reagents for quantifying oxidative stress-responsive gene induction, cellular stress gene induction, and/or NF-κB activation; apparatus and/or reagents for quantifying reactive oxygen species (ROS) production and/or glutathione depletion; apparatus and/or reagents for performing low-, medium-, or high-throughput screening assays as described herein; biological samples; reagents for isolating biological samples; sample tubes, holders, trays, racks, dishes, plates, solutions, buffers or other chemical reagents; needles or other consumables for administering the compounds of the invention; and suitable samples to be used for standardization, normalization, and/or control samples. Kits of the present invention can also be packaged for convenient storage and safe shipping, for example, in a box having a lid.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing digitized video or digitized optical images.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g., by fluorescent or dark field microscopic techniques.

VII. Methods of Selectively Inducing Oxidative Stress in a Cell

In another aspect, the invention provides methods of selectively inducing an oxidative stress response in a cell, the method comprising: contacting a cell with a selective heme oxygenase-1 (HMOX1) inducer, where the selective HMOX1 inducer is a non-naturally-occurring organic compound.

In some embodiments, the non-naturally-occurring organic compound is also a small organic compound, as defined above. In some such embodiments, the non-naturally-occurring organic compound is any of the compounds recited in Table 4, below, or a pharmaceutically acceptable salt thereof. In some other such embodiments, the non-naturally-occurring organic compound is any of the compounds recited as Examples in U.S. Patent Application Publication No. 2011/0201604, published Aug. 18, 2011.

In some further embodiments, the contacting of the cell occurs in vivo, for example, by administering the selective HMOX1 inducer, or a prodrug thereof, to a mammalian subject by any suitable means (e.g., oral, nasal, subcutaneous, intravenous, etc.). In some such embodiments, the mammalian subject is a human. In some other embodiments, the contacting of the cell occurs ex vivo, for example, in an in vitro assay.

In some further embodiments, the contacted cell is a cell selected from the group consisting of a lymphocyte, a granulocyte, a monocyte, a macrophage, a mast cell, a thrombocyte, an erythrocyte, a megakaryocyte, a dendritic cell, a glial cell, a pneumocyte, a Clara cell, a goblet cell, a myocardiocyte, a pericyte, a hepatocyte, a Kupffer cell, a Paneth cell, an osteoblast, an osteocyte, a chondroblast, a chondrocyte, a keratinocyte, a melanocyte, a myocyte, an adipocyte, a fibroblast, a tendon cell, an epithelial cell, an endothelial cell, a smooth muscle cell, a skeletal muscle cell, an embryonic stem cell, a neural stem cell, a skin stem cell, a mesenchymal stem cell, a hematopoietic stem cell, a stromal stem cell, or an epithelial stem cell. In some such embodiments, the cell is a mesenchymal stem cell. In other such embodiments, the cell is an osteocyte. In other such embodiments, the cell is a chondrocyte. In other such embodiments, the cell is an osteoblast. In other such embodiments, the cell is a chondroblast. In other such embodiments, the cell is an adipocyte. In other such embodiments, the cell is an endothelial cell. In other such embodiments, the cell is an epithelial cell. In other such embodiments, the cell is a myocardiocyte. In other such embodiments, the cell is an epithelial stem cell. In other such embodiments, the cell is a hematopoietic stem cell. In other such embodiments, the cell is a fibroblast.

EXAMPLES

The following examples are provided to illustrate, but not to limit the claimed invention.

Example 1

Primary Screening Assay for Identification of Selective Inducers of HMOX1

Introduction

An approach was generated for identifying, optimizing, and progressing novel inducers of HMOX1 and other oxidative stress-responsive genes through a novel mechanism of action involving the modulation of Bach1 and Nrf2 activity. The product profile for an HMOX1 inducer is a compound that can induce HMOX1 and additional oxidative stress-responsive genes in target tissues; that does not act as an electrophile or otherwise serve to incite a stress response; that requires the presence of Nrf2 for action; and that interferes with the action of Bach1. The biological screening profile is depicted in Table 3. Once activity is shown in vivo, the compounds will then be used in a variety of models where oxidative stress plays a role to assess therapeutic potential.

TABLE 3

| | Biological screening profile for HMOX1 inducer | |
|---|---|---|
| Primary screen | HMOX1 induction | >10-fold induction with an $EC_{50}$ < CoPP |
| mRNA expression profiling | Phase II genes | Induction of TXNRD1 and NQO1 |
| | ER stress genes | No induction of GADD45A, ATF4, or HSPA6 |
| | Genotoxic stress genes | No induction of CDKN1A or MDM2 |
| | NF-κB | No induction of NF-κB regulated genes (e.g., ICAM) |
| Cellular redox status | ROS production | Low elevation of cellular ROS; little to no loss of activity in the presence of N-acetyl cysteine (NAC) |
| | Glutathione depletion | No lowering of cellular glutathione |
| siRNA and gene silencing | Nrf2 dependence | Gene expression requires Nrf2 |
| | Keap1 dependence | Gene expression does not require Keap1 |

Materials and Methods

Preparation of Test Compounds

Test Compound 1: 3-Iodo-4-(2-methyl-tetrahydro-furan-3-ylsulfanyl)-quinoline may be prepared from 4-chloro-3-iodo-quinoline using the following procedure. To a 1:1 THF-1,4-dioxane solution of 4-chloro-3-iodo-quinoline may be added 2-methyl-3-tetrahydrofuranthiol, followed by cesium carbonate. The reaction mixture may be heated at 90° C. for 4 hours, then at ambient temperature overnight until thin layer chromatography analysis (4:1 hexanes-ethyl acetate eluent) shows a complete consumption of the starting material. The reaction may then be diluted with ethyl acetate and water, the phases separated, and the aqueous extracted 2 times with ethyl acetate. The combined organics may be dried over sodium sulfate, filtered, and the solvent evaporated. The crude material was purified using silica gel chromatography eluting with 9:1 hexanes-EtOAc to provide 4:1 hexanes-ethyl acetate 3-iodo-4-(2-methyl-tetrahydro-furan-3-ylsulfanyl)-quinoline.

This material may be dissolved in anhydrous dimethylformamide (DMF), to this solution added palladium acetate (5% mol), potassium acetate, tetrabutylammonium chloride, and ethyl acrylate. The reaction mixture may be heated to 110° C. and stirred at this temperature for 16 hours. Upon completion of the reaction, the mixture may be poured into saturated ammonium chloride solution and extracted with ethyl acetate. The organic extracts may be combined, washed with water and brine, dried over sodium sulfate and concentrated under vacuum. This residue may then be purified with silica gel chromatography using hexanes:ethyl acetate (from 95:5 to 70:30) as eluent system to give (E)-3-[4-(2-methyl-tetrahydro-furan-3-sulfanyl)-quinolin-3-yl]-acrylic acid ethyl ester.

(E)-3-[4-(2-Methyl-tetrahydro-furan-3-sulfonyl)-quinolin-3-yl]-acrylic acid ethyl ester may be prepared from (E)-3-[4-(2-methyl-tetrahydro-furan-3-sulfanyl)-quinolin-3-yl]-acrylic acid ethyl ester using the following the procedure. To a solution of the sulfanyl ester in dichloromethane may be added peracetic acid (2 eq., 32% wt in acetic acid) at 0° C. and stirred for 2-4 hours. The mixture is allowed to warm up to room temperature while stirring. After completion of the reaction, the mixture is poured into saturated sodium bicarbonate solution, and extracted with dichloromethane. The organic extracts are combined, washed with water, and brine solution and concentrated under vacuum to give the crude product. The concentrated residue may then be purified with silica gel chromatography using hexanes:ethyl acetate as an eluent (from 80:20 to 50:50) to afford (E)-3-[4-(2-methyl-tetrahydro-furan-3-sulfonyl)-quinolin-3-yl]-acrylic acid ethyl ester. LCMS: m/z 377 [M+2].

Test Compound 2: Test Compound 2 may be prepared by using procedures analogous to those used to prepare Test Compound 3 and using only 1 equivalent of peracetic acid.

Test Compound 3: 3-(4-trifluoromethyl-phenyl)-4-(2-methyl-tetrahydro-furan-3-sulfonyl)-quinoline may be prepared from 3-iodo-4-(2-methyl-tetrahydro-furan-3-ylsulfanyl)-quinoline and (4-trifluoromethyl-phenyl)boronic acid using following procedures.

To a DME solution of 3-iodo-4-(2-methyl-tetrahydro-furan-3-ylsulfanyl)-quinoline may be added 4-trifluoromethylphenyl)boronic acid, followed by 2N sodium carbonate and Pd(PPh$_3$)$_4$ (0.02 mmol). The reaction may be heated at 90° C. for 16 hours until LC/MS analysis shows a complete consumption of the starting material. After returning to ambient temperature and filtering, the solvent may be evaporated. The crude material may be purified using silica gel chromatography yielding 3-(4-trifluoromethyl-phenyl)-4-(2-methyl-tetrahydro-furan-3-ylsulfanyl)-quinoline.

To a solution of the sulfanyl ester in dichloromethane may be added peracetic acid (2 eq., 32% wt in acetic acid) at 0° C. and stirred for 2-4 hours. The mixture is allowed to warm up to room temperature while stirring. After completion of the reaction, the mixture may be poured into saturated sodium bicarbonate solution (50 mL), and extracted with dichloromethane. The organic extracts are combined, washed with water, and brine solution, and concentrated under vacuum to give the crude product. The concentrated residue may then be purified with silica gel chromatography using hexanes: ethyl acetate as an eluent (from 80:20 to 50:50) to afford 3-(4-trifluoromethyl-phenyl)-4-(2-methyl-tetrahydro-furan-3-sulfonyl)-quinoline. LC/MS: m/z 423 [M+2].

Test Compound 4: Test Compound 4 may be prepared using procedures analogous to those used to prepare Test Compounds 8, 9, and 10 and using 3,4-diamino-benzoic acid methyl ester and 2-amino-benzothiazole.

Test Compound 5: Test Compound 5 (also known as Oleana-2,9(11)-dien-28-oic acid, 2-cyano-3-hydroxy-12-oxo-, methyl ester) may be prepared as disclosed in WO2009/146216 and as referenced in J. Med. Chem. "Synthetic Oleanane and Ursane Triterpenoids with Modified Rings A and C: A Series of Highly Active Inhibitors of Nitric Oxide Production in Mouse Macrophages" (2000), vol. 42, pp. 4233-4246.

Test Compound 6: Test Compound 6 may be prepared using procedures analogous to those used to prepare Test Compounds 8, 9, and 10 and as modified accordingly.

Test Compound 7: Test Compound 7 may be prepared using procedures analogous to those used to prepare Test Compounds 8, 9, and 10 and as modified accordingly.

Test Compound 8: 1-Methyl-2-(6-trifluoromethoxy-benzothiazol-2-ylamino)-1H-benzoimidazole-5-carboxylic acid methyl ester may be prepared from 3-amino-4-methyl-amino-benzoic acid methyl ester, 2-amino-6-(trifluoromethoxy)benzothiazole, 1,1'-thiocarbonyl-diimidazole, and 1-ethyl-3-(3-dimethylaminopropyl)carbodiimide (EDC). 1,1'-Thiocarbonylimidazole may be added to a solution of 2-amino-6-(trifluoromethoxy)benzothiazole in DMF, and the reaction mixture stirred at 90-100° C. for a day. To this reaction mixture at room temperature is added EDC and stirred at 60° C. for 5 min. To this reaction mixture at room temperature is added 3-amino-4-methylamino-benzoic acid methyl ester and stirred at 90° C. The reaction mixture may then be cooled to room temperature, poured into ice-cold water and the solid collected by filtration. The crude product thus obtained may be purified by trituration with dichloromethan-methanol (9:1). LC/MS: m/z 423.8 (M+1)$^+$.

1-Methyl-2-(6-trifluoromethoxy-benzothiazol-2-ylamino)-1H-benzoimidazole-5-carboxylic acid may be prepared by following from 1-methyl-2-(6-trifluoromethoxy-benzothiazol-2-ylamino)-1H-benzoimidazole-5-carboxylic acid methyl ester and lithium hydroxide. A solution of LiOH in water may be added to a solution of the ester in 1:1 THF/MeOH and the resulting mixture stirred at 60° C. After completion of the reaction, the mixture may be concentrated under vacuum, and the pH of the resulting suspension would be adjusted by the dropwise addition of 6 N HCl to pH ~3. The precipitate may be collected by filtration, washed with water and dried under vacuum. The desired carboxylic acid may be used without further purification. LC/MS: m/z 409.9 (M+1)$^+$.

1-Methyl-2-(6-trifluoromethoxy-benzothiazol-2-ylamino)-1H-benzo-imidazole-5-carboxylic acid (2-methoxy-ethyl)-amide may be prepared from 1-methyl-2-(6-trifluoromethoxy-benzothiazol-2-ylamino)-1H-benzo-imidazole-5-carboxylic acid, 2-methoxy-ethylamine, diphenylphosphoryl azide (DPPA), and diisopropylethylamine (DIEA). To a solution of a carboxylic acid in dry dimethyl formamide (DMF) may be added DIEA followed by DPPA and the reaction mixture stirred at room temperature for 30 min. The 2-methoxy-ethylamine may then be added, and the reaction stirred at room temperature for 2 hours. The contents may then be diluted with ice water and the product precipitated. The product may be isolated after filtration either with subsequent washings with water and dichloromethane/methanol or through silica gel chromatography using hexanes/ethyl acetate as eluent.

LC/MS: m/z 466.9 (M+1)$^+$. $^1$H NMR (DMSO-d$_6$, 400 MHz): δ 12.36 (bs, 1H), 8.47 (s, 1H), 8.08 (s, 1H), 7.89 (s,

1H), 7.76 (s, 1H), 7.71 (d, 1H), 7.47 (d, 1H), 7.34 (d, 1H), 3.62 (bs, 3H), 3.53-3.38 (m, 4H), 3.27 (s, 3H).

Test Compound 9: 1-Methyl-2-(6-trifluoromethoxy-benzothiazol-2-ylamino)-1H-benzoimidazole-5-carboxylic acid dimethylcarbamoylmethyl-amide may be prepared from 1-methyl-2-(6-trifluoromethoxy-benzothiazol-2-ylamino)-1H-benzimidazole-5-carboxylic acid, 2-amino-N,N-dimethyl-acetamide, 2-(1H-benzotriazol-1-yl)-1,1,3,3-tetramethyluronium hexafluorophosphate (HBTU), and DIEA.

To a solution of the carboxylic acid in dry DMF may be added DIEA followed by HBTU, and the reaction mixture stirred at room temperature for 30 min. The 2-amino-N,N-dimethyl-acetamide may then be added, and the reaction stirred at room temperature for 16 hours. The contents may be diluted with ice water, and the product precipitated. The product may be isolated after filtration either with subsequent washings with water and dichloromethane/methanol or through silica gel chromatography using hexanes/ethyl acetate (from 80:20 to 60:40) as an eluent system.

LC/MS: m/z 494 [M+2]. $^1$H NMR (DMSO-$d_6$, 400 MHz): δ 8.42 (t, 1H), 8.09 (s, 1H), 7.90 (m, 1H), 7.78 (br, 1H), 7.72 (br, 1H), 7.48 (d, 1H), 7.44 (d, 1H), 7.34 (m, 1H), 4.11 (d, 2H), 3.63 (s, 3H), and 3.00 (d, 6H).

Test Compound 10: 1-Methyl-2-(6-trifluoromethoxy-benzothiazol-2-ylamino)-1H-benzoimidazole-5-carboxylic acid [2-(2-hydroxy-ethoxy)-ethyl]-amide may be prepared from 1-methyl-2-(6-trifluoromethoxy-benzothiazol-2-ylamino)-1H-benzimidazole-5-carboxylic acid (250 mg), 2-(2-aminoethoxy)ethanol, HBTU, and DIEA using a procedure similar to that used to prepare Test Compound 9.

LC/MS: m/z 496.8 (M+1)$^+$. $^1$H NMR (DMSO-$d_6$, 400 MHz): δ 12.39 (bs, 1H), 8.47 (t, 1H), 8.09 (s, 1H), 7.91 (s, 1H), 7.78 (d, 1H), 7.73 (d, 1H), 7.49 (d, 1H), 7.36 (d, 1H), 4.61 (t, 1H), 3.64 (s, 3H), 3.57 (t, 2H), 3.51 (t, 2H), 3.49-3.41 (m, 4H).

Test Compounds 11, 12, and 13: Test Compounds 11, 12, and 13 may be prepared using procedures analogous to those used to prepare Test Compounds 8, 9, and 10 and as modified accordingly.

Test Compounds 14 and 15: Test Compounds 14 and 15 may be prepared as disclosed in WO2007/089257. See Example 140 on pages 148 to 149.

Cell Culture

Normal Human Lung Fibroblast (NHLF) were obtained from Lonza. Cultures of cells were maintained in Fibroblast Growth Medium (FGM-2) medium supplemented with 2% fetal bovine serum (FBS), fibroblast growth factor (hFGF-B) 0.5 ml, insulin 0.5 ml, and gentamicin/amphotericin-B 0.5 mL at 37° C. in a humidified atmosphere of 5% $CO_2$. Primary isolates of cell were cultured in T-225 flasks (Corning) as per instructions from the vendor. Cells were grown to 80% confluence before harvesting. Cells were harvested by first washing with 5 mL of Hepes buffered saline solution (Lonza). The buffered salt solution was aspirated and then 5 mL of a solution of Trypsin-EDTA was added to detach the cells from the culture flask. To this mixture 5 mL of Trypsin neutralization solution (Lonza) was added. The mixture was centrifuged at 500× g for 10 minutes at 4° C. The cell pellet was resuspended to a final concentration of one million cells per milliliter in fetal bovine serum containing 6% DMSO. The cells were then dispensed into cryovials and frozen in liquid nitrogen for storage.

mRNA Expression

Secondary growth of NHLF cells were used for all assays. Cell were thawed and then placed into culture in T225 flasks. The cells were grown to 80% confluency and harvested by washing once with HEPES buffered saline solution and then trypsinizing. Equal numbers ($7 \times 10^3$ cells per well) of NHLF cells were plated in 96 well tissue culture plates (Corning). Cells were incubated overnight in FGM-2 medium prior to exposure to compound. Cells were treated with either DMSO or a compound as described below for 6 h. Preparation of cell lysates was carried out according to instructions using the Quantigene Reagent system 2.0 protocol (Panomics). mRNA induction was detected from cell lysate using the Quantigene Plex 2.0 Assay Kit (Panomics) on the Luminex platform (BIO-RAD). Expression of GAPDH mRNA was used as the internal control for the Quantigen Plex 2.0 Assay. The data in Tables 5 and 6 represents the fold change of target mRNA expression, normalized to control values, above DMSO treated cells.

HMOX1 Protein Expression

NHLF cells were grown to 80% confluency and harvested by washing once with HEPES and then trypsinizing. Equal numbers ($7 \times 10^4$ cells per well) of NHLF cells were plated in 384 well optilux tissue culture (BD) plates. Cells were incubated overnight in FGM-2 medium prior to exposure to compound. Cells were treated with either DMSO or compound for 16 h. Cells were wash 2× with 1×PBS and fix with 4% Paraformaldyhyde for 15 min. The fixed cells were then permeablized with 0.1% Triton X-100 and blocked with 5% BSA in 1× PBS 0.05% Tween-20 for 15 min. HO-1 antibody (abcam) was used for immunostaining at 1:300 dilution in 1% BSA in 1×PBS for 1 hr. Cells were washed 2× with 1×PBS and secondary antibody goat anti-mouse Alexa 488 1:400 dilution (Invitrogen); Hoechst 1:2000 (Invitrogen) in 1% BSA in 1×PBS for 1 hr. The plate was washed 5× with 1×PBS and read at Hoechst Excitation ("Ex.") 360 Emission ("Em.") 535; Alexa 488 Ex. 480 Em. 535 using GE InCell 1000. Results were analyzed using GE InCell Analyzer software and represented as the fold change above DMSO treated cells.

ROS Measurements

Secondary growth of NHLF cells were used for all assays. Cells were cultured as above. Cells were plated into 384-well BD-Optilux Plates at 2,000 cells/well and cultured overnight at 37° C. and 5% $CO_2$. The following day, cell were washed and 2,7-dihydrodichlorofluorescin diacetate (H2DCF-DA), 10 μM ferric ammonium citrate (FAC), and Hoechst stain were added to cells for 30 min. The cells were washed once with PBS to remove any H2DCF-DA not taken up by cells. Test compounds were prepared in FBM-2 media at the desired concentrations. The plates and stain-treated cells were incubated with test compounds for 1 hr at 37° C. and 5% $CO_2$. Following the incubation period, ROS generation was determined by imaging the cells on a GE INcell 1000 imager (Hoechst Ex. 360 Em. 535; H2DCF-DA 488 Ex. 480 Em. 535). ROS levels were determined and quantified using GE IN Cell Analyzer Software.

Effect of NAC on Compound Induction of HMOX Gene Expression

NHLF cells were grown to 80% confluency and harvested by washing once with HEPES and then trypsinizing. Equal numbers ($7 \times 10^4$ cells per well) of NHLF cells were plated in 96 well tissue culture (Corning) plates. Cells were incubated overnight in FGM-2 medium prior to exposure to compound. Cells were pretreated with 5 mM N-acetyl cysteine for 1 hr. Cells were treated with either DMSO or compound for 6 h. Preparation of cell lysates was carried out according to Quantigene Reagent system 2.0 protocol (Panomics). Heme oxygenase mRNA induction was detected from cell lysate using the Quantigene Plex 2.0 Assay Kit (Panomics) on the Luminex platform (BIO-RAD). Expression of GAPDH mRNA was used as the internal control for the Quantigen Plex 2.0 Assay. Heme oxygenase data represents the fold change, normalized to control values, above DMSO treated cells.

siRNA

Small interfering RNA targeting Nrf-2 (cat# SI03246614) or KEAP-1 (cat# SI03246439) were obtained from Qiagen at 20 nmol/tube. Negative control siRNA (cat#1027280) was also obtained from Qiagen. Lyophilized siRNA in each tube was resuspended with 1 ml of the provided siRNA Suspension Buffer to make a stock solution of 20 μM and tubes were heated at 90° C. for one minute and then at 37° C. for one hour prior to initial use.

Normal human lung fibroblasts were plated at 5000 cells/well in 96-well plates and allowed to attach. Prior to experiments, well s containing the cells were refreshed with 30 μl of complete growth medium. For each siRNA type, a 4× concentration (200 nM) of siRNA was prepared by adding 11 μl of siRNA stock into 1.1 ml of serum-free medium containing 9 μl/ml of SILENTFECT Lipid Reagent (BioRad, cat#170-3361). This solution was incubated at room temperature for 20 minutes prior to adding 10 μl into each well for a final concentration of 50 nM siRNA. Cells were incubated with siRNA for 48 hours, after which they were treated with compound for either 5 hours (QuantiGene RNA assay) or 15 hours (protein immunofluorescence assay).

Lentiviral Particles shRNA

Normal human lung fibroblasts were plated in a 12-well tissue culture dish at 16,000 cells/well and allowed to attach overnight. Regular medium was then replaced with 200 μl of fresh growth medium containing 8 μg/ml hexadimethrine bromide (polybrene). Lentiviral transduction particles were then added in the following amounts: Control shRNA (1.1× $10^7$ TU/ml, Sigma, cat# SHC002V), 15 μl for an MOI of 10; KEAP-1 shRNA (6.3×$10^6$ TU/ml, Sigma, cat# SHCLNV-TRCN0000046092), 63 μl for an MOI of 20. After 4 hours in the cell culture incubator, another 200 μl of growth medium was added on top of the original volume. Cells were replenished the next day with fresh complete growth medium and were allowed to recover for 24 hours, after which selection medium was applied (complete medium with 1 μg/ml puromycin).

Results

Figure 2:
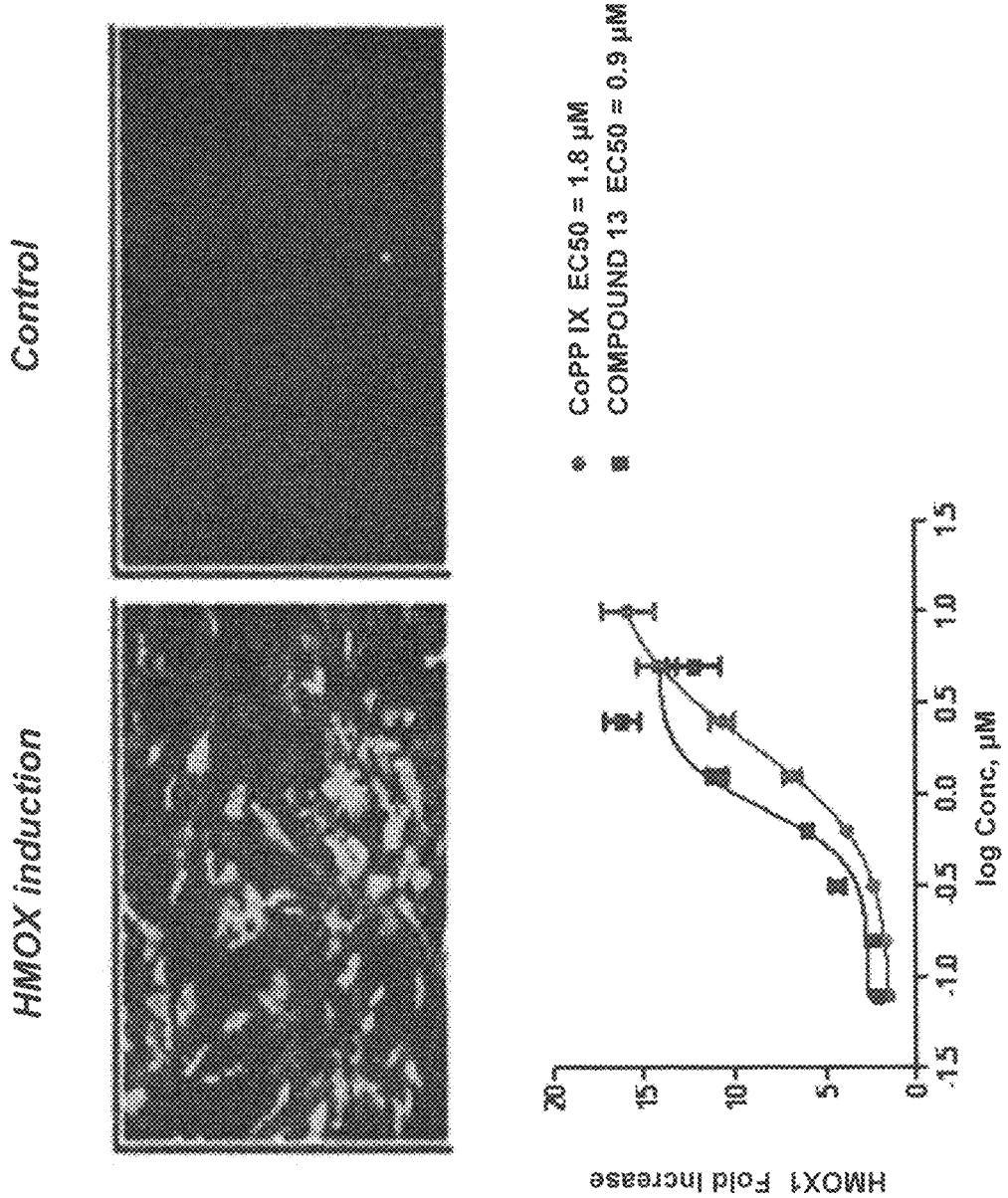
FIG. 2. Characterization of Compound 13 induction of HMOX1. The photos in the upper panel represent captured immunofluorescent image data comparing and demonstrating the induction of HMOX1 in normal human lung fibroblast (NHLF) cells following exposure to test compounds. An example of a full dose response curve for the control compound cobalt protoporphyrin (CoPP) and for Compound 13, a screening hit, are shown in the lower panel.

A rapid, quantitative screening assay to detect HMOX1 levels in cells based on an immunofluorescent microscopy using an automated high-content imaging system was developed. A collection of 400,000 compounds of a variety of chemical structures and pharmacophores was screened including the compounds identified in Table 4. The cell type chosen was a primary normal human lung fibroblast. Using such a method we identified a number of compounds from the TransTech Pharma's TTPROBES® collection that were potent inducers of HMOX1. A representative plate with numerical representation of the data is shown in FIG. 1. The data are arranged along the X-axis as the well coordinate and the Y-Axis is the averaged signal intensity for HMOX1 staining in the cells. The data are arrayed as in an IR chart with a calculated mean value for the plate and the 3-sigma upper and lower-confidence limits (UCL and LCL). Any value appreciably above the UCL was considered an active molecule. Each hit was then subsequently screened for potency as compared to a control compound, in this case the metalloporphyrin cobalt protoporphyrin (CoPP). One such hit, labeled Compound 13, was subsequently characterized and shown to have an effective potency of less than 1 μM (FIG. 2).

TABLE 4

Test compounds

| Compound number | Compound structure | Compound name |
| --- | --- | --- |
| 1 | 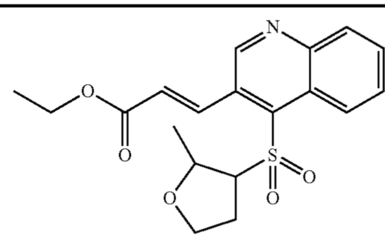 | (E)-3-[4-(2-Methyl-tetrahydro-furan-3-sulfonyl)-quinolin-3-yl]-acrylic acid ethyl ester |
| 2 | 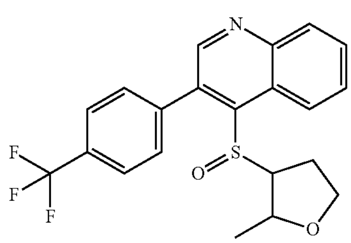 [SMILES: CC1OCCC1S(=O)c1c(-c2ccc(C(F)(F)F)cc2)cnc2ccccc12] | 4-(2-Methyl-tetrahydro-furan-3-sulfonyl)-3-(4-trifluoromethyl-phenyl)-quinoline |
| 3 | 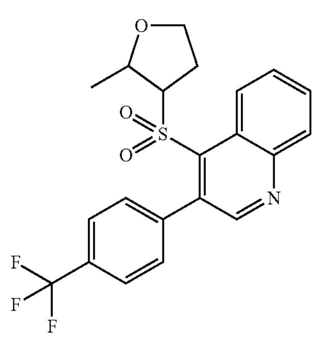 [SMILES: CC1OCCC1S(=O)(=O)c1c(-c2ccc(C(F)(F)F)cc2)cnc2ccccc12] | 4-(2-Methyl-tetrahydro-furan-3-sulfonyl)-3-(4-trifluoromethyl-phenyl)-quinoline |

TABLE 4-continued

Test compounds

| Compound number | Compound structure | Compound name |
|---|---|---|
| 4 | 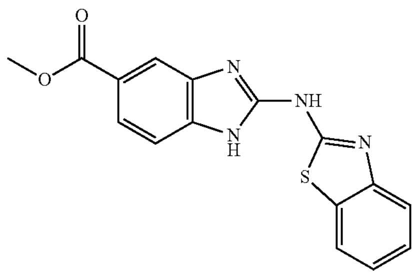 [SMILES: COC(=O)c1ccc2[nH]c(Nc3nc4ccccc4s3)nc2c1] | 2-(Benzothiazol-2-ylamino)-1H-benzoimidazole-5-carboxylic acid methyl ester |
| 5 | 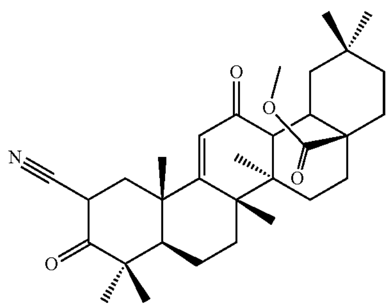 | (4aS,6aR,6bS,8aR,12aS)-11-Cyano-2,2,6a,6b,9,9,12a-heptamethyl-10,14-dioxo-1,3,4,5,6,6a,6b,7,8,8a,9,10,11,12,12a,14,14a,14b-octadecahydro-2H-picene-4a-carboxylic acid methyl ester |
| 6 | 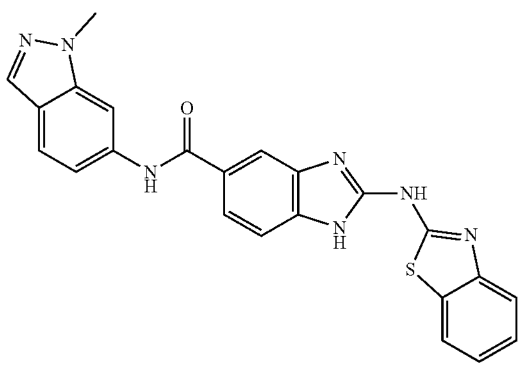 [SMILES: Cn1ncc2ccc(NC(=O)c3ccc4[nH]c(Nc5nc6ccccc6s5)nc4c3)cc21] | 2-(Benzothiazol-2-ylamino)-1H-benzoimidazole-5-carboxylic acid (1-methyl-1H-indazol-6-yl)-amide |
| 7 | 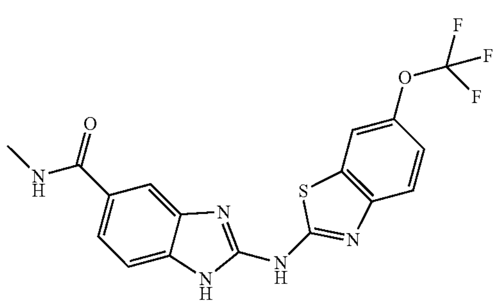 [SMILES: CNC(=O)c1ccc2[nH]c(Nc3nc4ccc(OC(F)(F)F)cc4s3)nc2c1] | 2-(6-Trifluoromethoxy-benzothiazol-2-ylamino)-1H-benzoimidazole-5-carboxylic acid methylamide |

TABLE 4-continued

| Test compounds | | |
|---|---|---|
| Compound number | Compound structure | Compound name |
| 8 | 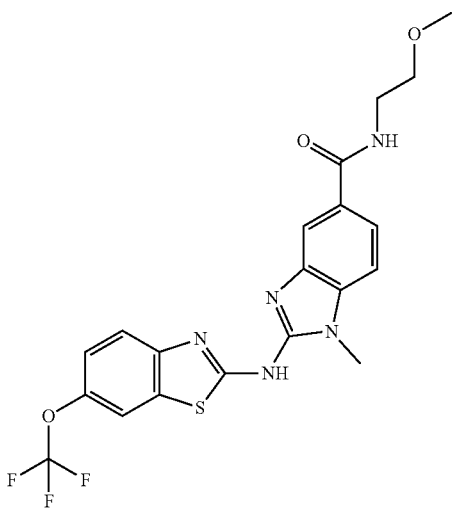 [SMILES: COCCNC(=O)c1ccc2c(c1)nc(Nc1nc3ccc(OC(F)(F)F)cc3s1)n2C] | 1-Methyl-2-(6-trifluoromethoxy-benzothiazol-2-ylamino)-1H-benzoimidazole-5-carboxylic acid (2-methoxy-ethyl)-amide |
| 9 | 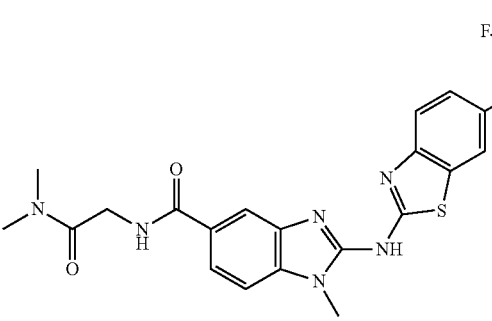 | 1-Methyl-2-(6-trifluoromethoxy-benzothiazol-2-ylamino)-1H-benzoimidazole-5-carboxylic acid (2-methoxy-ethyl)-amide |
| 10 | 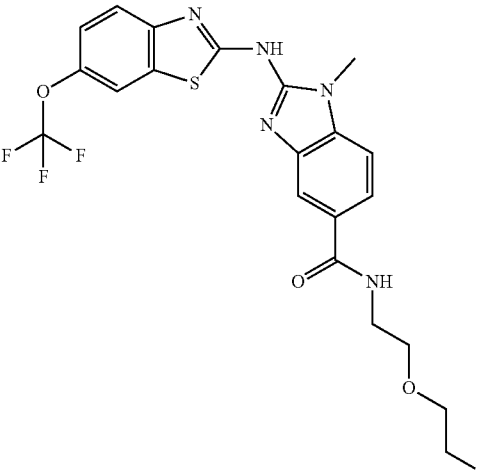 | 1-Methyl-2-(6-trifluoromethoxy-benzothiazol-2-ylamino)-1H-benzoimidazole-5-carboxylic acid [2-(2-hydroxy-ethoxy)-ethyl]-amide |

TABLE 4-continued

| Compound number | Compound structure | Compound name |
|---|---|---|
| 11 | 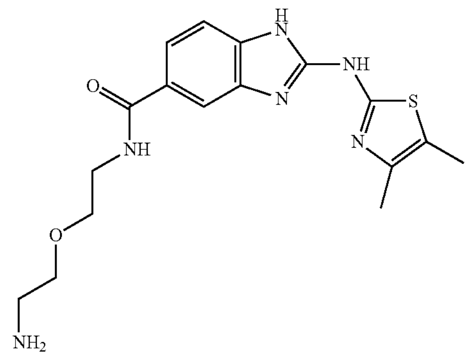 [SMILES: Cc1nc(Nc2nc3cc(C(=O)NCCOCCN)ccc3[nH]2)sc1C] | 2-(4,5-Dimethyl-thiazol-2-ylamino)-1H-benzoimidazole-5-carboxylic acid [2-(2-amino-ethoxy)-ethyl]-amide |
| 12 | 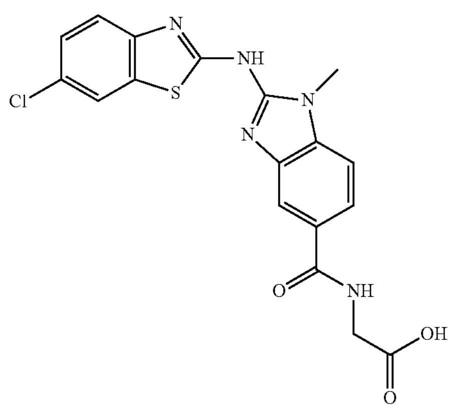 [SMILES: Cn1c(Nc2nc3ccc(Cl)cc3s2)nc2cc(C(=O)NCC(=O)O)ccc21] | {[2-(6-Chloro-benzothiazol-2-ylamino)-1-methyl-1H-benzoimidazole-5-carbonyl]-amino}-acetic acid |
| 13 | 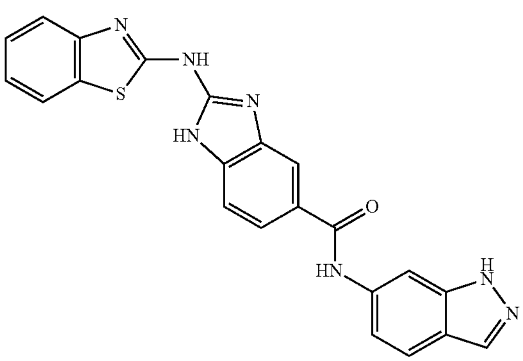 [SMILES: O=C(Nc1ccc2cn[nH]c2c1)c1ccc2[nH]c(Nc3nc4ccccc4s3)nc2c1] | 2-(Benzothiazol-2-ylamino)-1H-benzoimidazole-5-carboxylic acid (1H-indazol-6-yl)-amide |
| 14 | 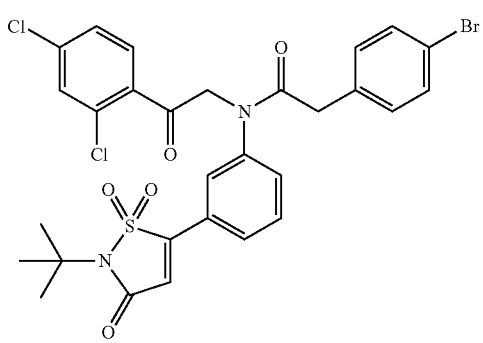 [SMILES: CC(C)(C)N1C(=O)C=C(c2cccc(N(CC(=O)c3ccc(Cl)cc3Cl)C(=O)Cc3ccc(Br)cc3)c2)S1(=O)=O] | 2-(4-Bromo-phenyl)-N-[3-(2-tert-butyl-1,1,3-trioxo-2,3-dihydro-1H-isothiazol-5-yl)-phenyl]-N-[2-(2,4-dichloro-phenyl)-2-oxo-ethyl]-acetamide |

TABLE 4-continued

Test compounds

| Compound number | Compound structure | Compound name |
|---|---|---|
| 15 | 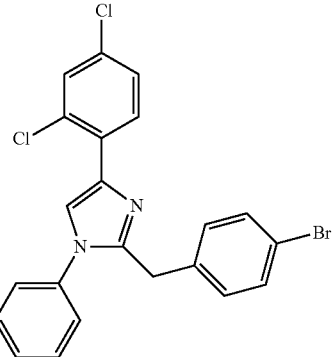 | 5-{3-[2-(4-Bromo-benzyl)-4-(2,4-dichloro-phenyl)-imidazol-1-yl]-phenyl}-2-tert-butyl-1,1-dioxo-1,2-dihydro-isothiazol-3-one |

Figure 3A:
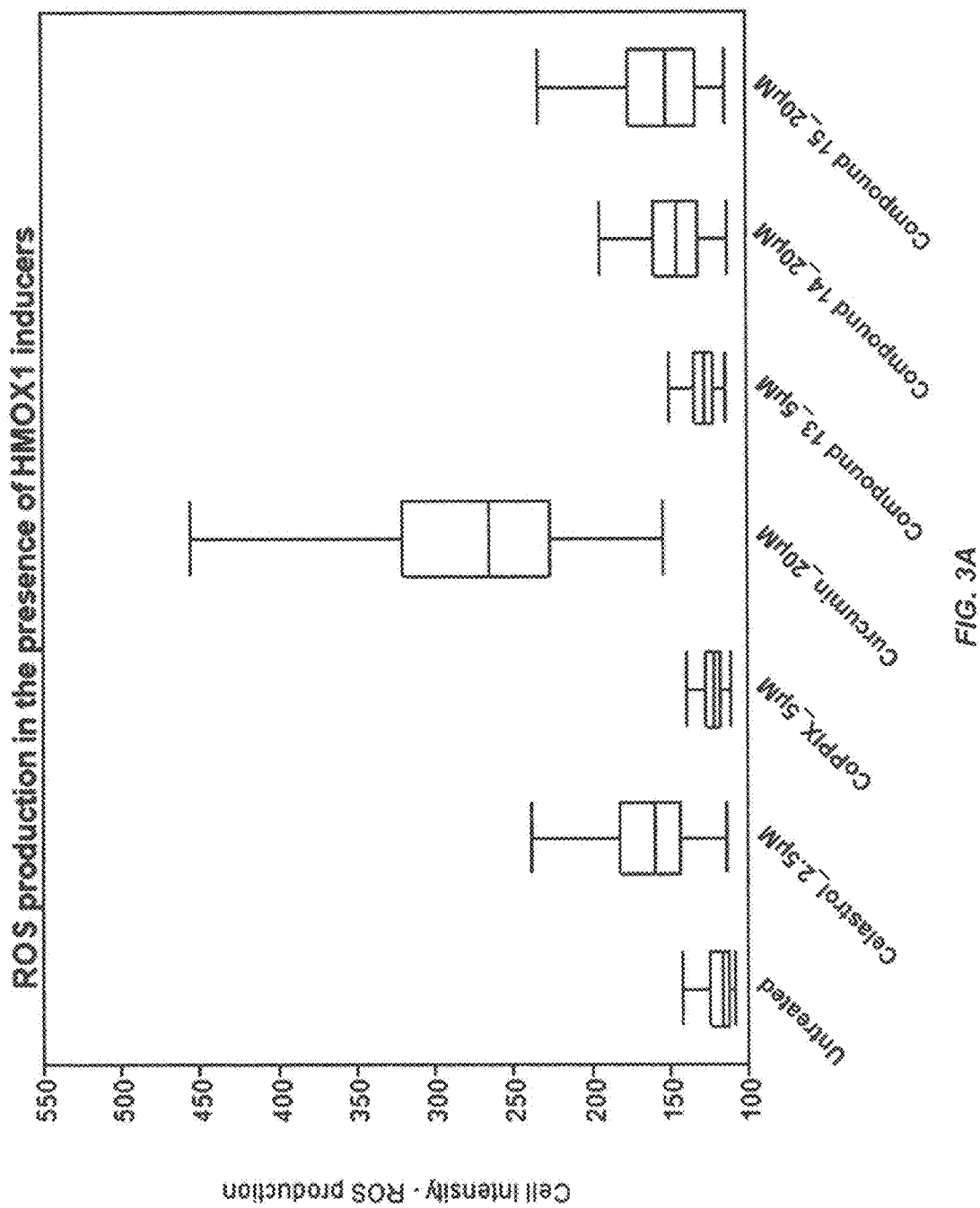
FIG. 3A is a graph showing Reactive oxygen species (ROS) induction in cells following exposure to indicated compounds.
Figure 3B:
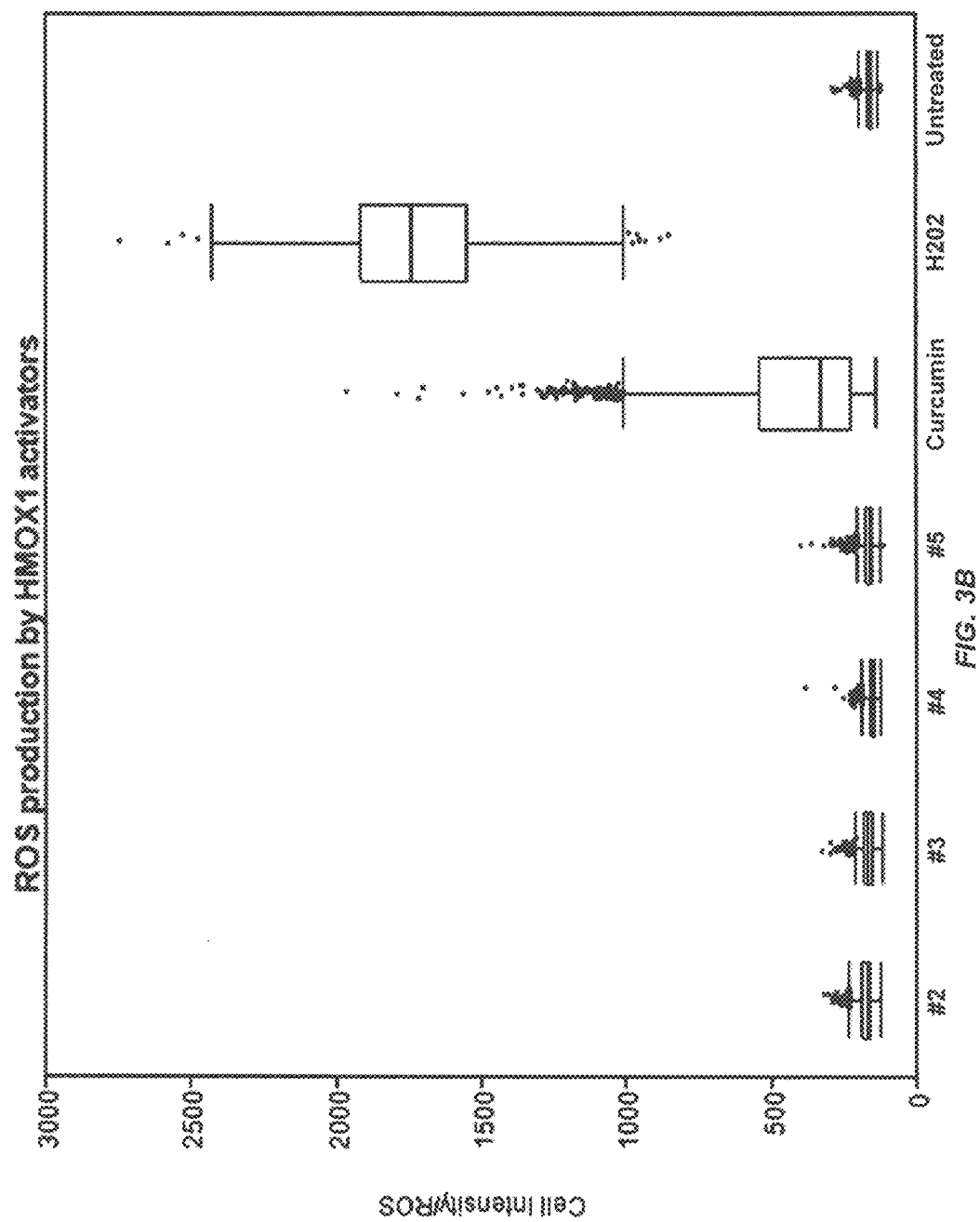
FIG. 3B is a graph showing ROS production in cells following exposure to a separate set of indicated compounds. ROS production is detected using a specific immunofluorescent agent and quantified. The graphs in (FIG. 3A) and (FIG. 3B) represent a cell-by-cell analysis of ROS generation under the influence of tool and test compounds.

In addition to gene profiling, the requirement for ROS generation or chemical reactivity was tested. ROS generation was measured using an automated imaging technique. Compound 13 as well as two other compounds that were found in the screening set were tested in this experiment. Untreated NHLF cells, NHLF cells treated with the HMOX1 inducer CoPP (a negative control), and NHLF cells treated with curcumin or celestrol (positive controls) were included as controls. Relative to control treatment, Compound 13 modestly elevated ROS production, but did so in a manner insignificant from CoPP and much less than the positive controls curcumin and celestrol. As shown in FIG. 3A, Compound 13 elevated ROS levels to the lowest degree, based on a Tukey-Kramer test. Curcumin and celestrol elevated ROS production approximately 3-fold and 2-fold, respectively, whereas CoPP did not, relative to untreated controls. Compound 14 and Compound 15, two additional screening hits, elevated ROS levels to a greater degree than did Compound 13. Further experiments were also conducted on chemical derivatives of Compound 13. In those experiments, all compounds tested were found not to induce an elevation of ROS levels in the cell (FIG. 3B). Thus, Compound 13 and related compounds represent a class of agents that elevate HMOX1 production without elevating ROS production.

Figure 4:
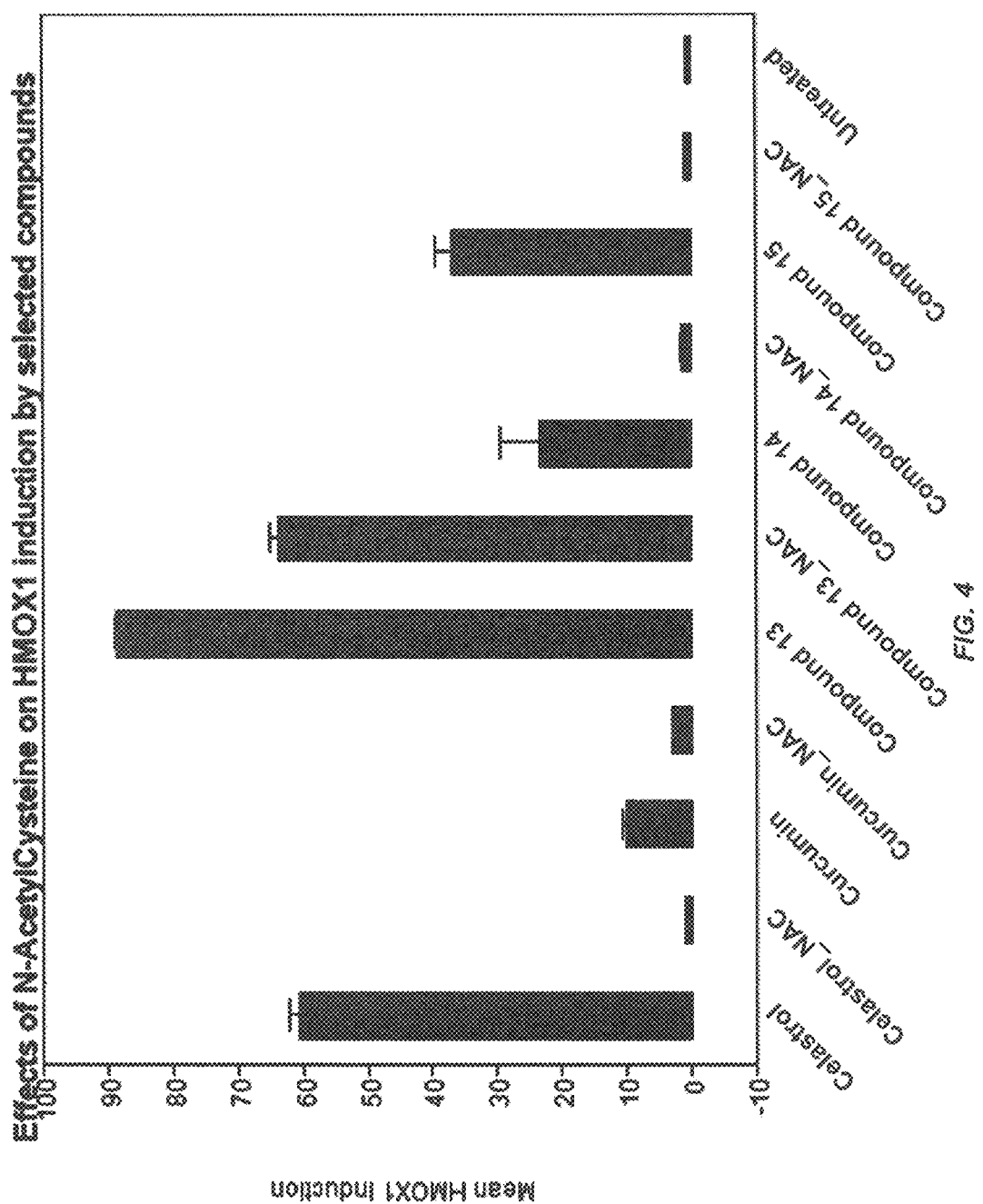
FIG. 4. Effect of N-acetylcysteine (NAC) on HMOX1 induction in normal human lung fibroblasts. NAC fully suppresses the induction of HMOX1 when induction is due to ROS generation or depletion of cellular glutathione.

A further test of the hypothesis that Compound 13 induces HMOX1 with minimal alteration of cellular redox levels or chemical reactivity was carried out by treating cells with N-acetyl cysteine (NAC). This compound acts to restore cellular glutathione levels and thus prevent oxidative stress. The degree to which NAC can suppress HMOX1 induction is an indicator of the amount of chemical reactivity or ROS stress that a compound is imposing on the cell and thus activating phase II gene transcription. As shown in FIG. 4, Compound 13 induces the greatest amount of HMOX1 with the least impact by NAC. Compound 14, Compound 15, and the positive controls curcumin and celestrol are inhibited nearly fully by NAC. Coupled with the data shown in FIG. 3, it is concluded that Compound 13 induces HMOX1 with minimal elevation of ROS or NAC-sensitive chemical reactivity.

Following identification of the hit Compound 13, a transcriptional profile was made to ascertain the ability of the compound to induce phase II genes to have no effect on the alternate pathways as described in Table 3. As shown in Table 5, Compound 13 was shown to induce other phase II genes such as NQO1 and TXNRD1. Compound 13 did not induce ER stress genes such as HSPA6 nor did it induce NF-κB regulated genes such as ICAM (Table 5). Additional experiments with chemical analogues revealed the ability of the transcriptional profile to differentiate compound activity. Four analogues of Compound 13 were tested for induction of gene expression patterns. Of the four, three showed a similar pattern of behavior as Compound 13. However, one compound, Compound 2, also highly induced HSPA6 and GADD45a, two genes related to cellular stress (Table 6).

TABLE 5

Compound 13 induces additional phase II genes, but does not induce ER, cellular, or genotoxic stress pathways and does not activate NF-κB

| | Gene (fold induction) | | | | | | |
|---|---|---|---|---|---|---|---|
| Compound | HMOX1 | NQO1 | TXNRD1 | HSPA6 | ICAM | ATF4 | GADD45A |
| CoPP | 48 | 3.5 | 2.7 | 0.9 | 1.1 | 0.85 | 1.02 |
| #13 | 25 | 2.2 | 1.5 | 0.96 | 1.1 | 1.2 | 0.89 |

TABLE 6

Chemical derivatives of Compound 13 induce phase II genes, but do not induce
ER, cellular, or genotoxic stress pathways and do not activate NF-κB

| | Gene (fold induction) | | | | | |
|---|---|---|---|---|---|---|
| Compound | HMOX1 | NQO1 | TXNRD1 | HSPA6 | GADD45A | ICAM1 |
| CoPP | 49.64 | 4.22 | 2.39 | 0.86 | 1.18 | 0.56 |
| #2 | 35.71 | 1.29 | 1.39 | 81.22 | 3.27 | 0.89 |
| #3 | 45.17 | 1.69 | 1.47 | 2.71 | 1.37 | 1.47 |
| #4 | 56.15 | 1.85 | 1.74 | 1.08 | 2.00 | 0.77 |
| #5 | 23.97 | 2.01 | 1.83 | 1.60 | 0.89 | 1.16 |

Compound 13 appears to induce HMOX1 independent of chemical reactivity or induction of cellular stress. Next, it was ascertained whether the induction of gene transcription is regulated by Nrf2. Gene silencing is an approach whereby a gene product's effects on a biological process can be assessed. Unlike the creation of a genetic null allele, where the entire gene product is missing or made non-functional, gene silencing merely reduces the level of protein in a manner that is time and dose dependent with treatment using a specific silencing RNA. In general, most gene silencing experiments do not result in the complete loss of a phenotype. Rather, it can be said that a full response depends on the gene product in question.

Figure 5:
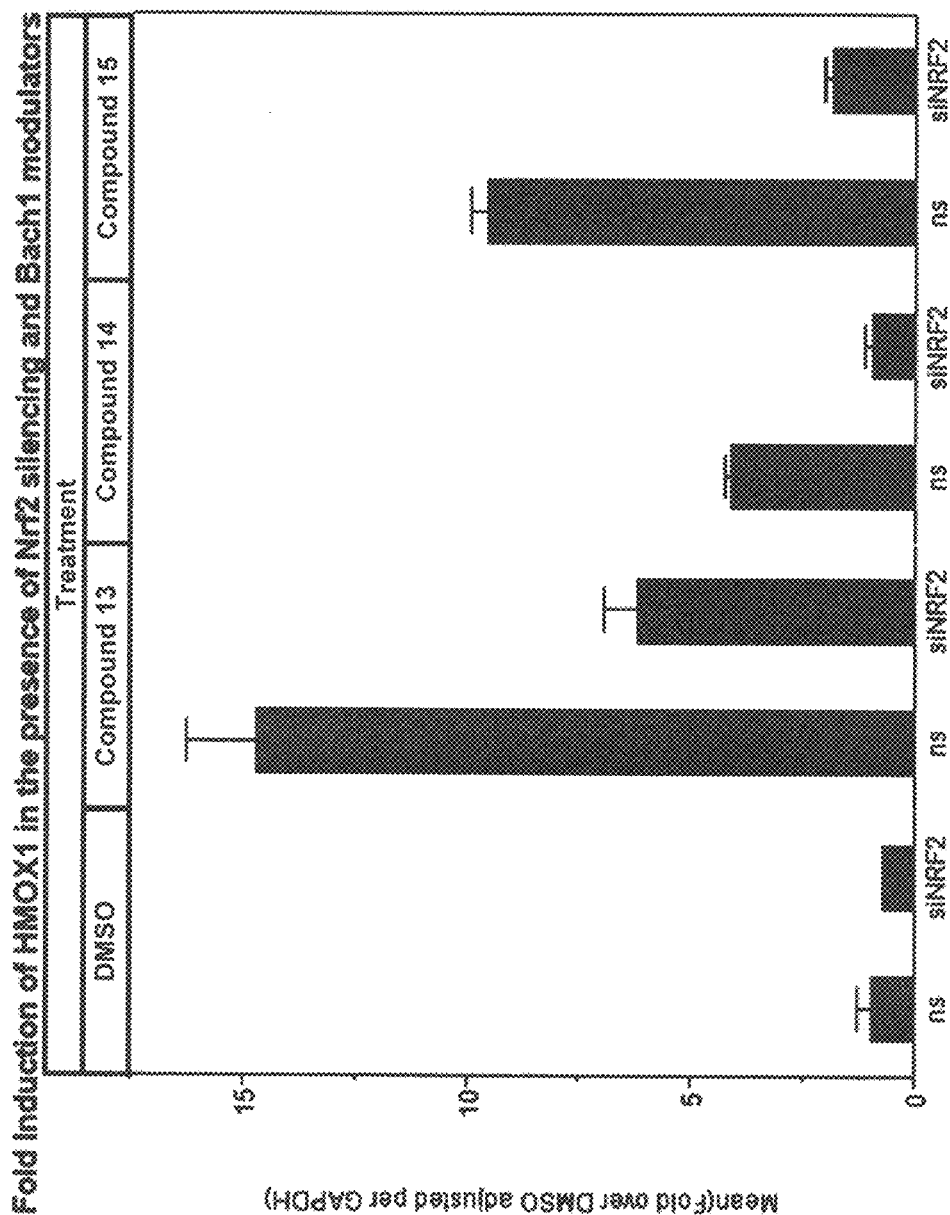
FIG. 5. Silencing of Nrf2 reduces the amount of HMOX1 expression by screening hits. NHLF cells treated with small interfering RNA (siRNA) directed to Nrf2 will suppress the induction of genes that require Nrf2 for activation.

The predicted response profile is that silencing of Nrf2 should reduce the amount of HMOX1 induction by Compound 13 and other HMOX1 inducers that are electrophiles or reactive compounds. To that end, Compound 13 and other tool compounds were tested in cells that were treated with siRNA directed to Nrf2. Following gene silencing with specific siRNA or control siRNA, the ability of tool compounds to induce HMOX1 mRNA was determined. Compound 13, Compound 14, and Compound 15 were all affected by the presence of the siRNA for Nrf2 (FIG. 5), indicating that each compound requires Nrf2 for maximal induction of HMOX1.

The demonstration that silencing of Nrf2 will lead to reduced production of HMOX1 by Compound 13 and tool compounds implicates Nrf2 in their activities. Another method of testing the role of the Nrf2 regulatory pathway on compound activity is to determine the effect of silencing Keap1 on HMOX1 gene expression. It is known that deleting Keap1 will result in the induction of Nrf2 dependent genes but not, to any significant degree, HMOX1. The proposed explanation for this observation is that HMOX1 requires the concomitant derepression of Bach1 activity and that this event is more dependent on active processes (e.g., heme binding, changes in redox potential of the cell, phosphorylation of Bach1, etc.). We therefore tested the ability of Compound 13 and tool compounds to induce HMOX1 in the presence of silencing of Keap1 in normal human lung fibroblasts.

Figure 6:
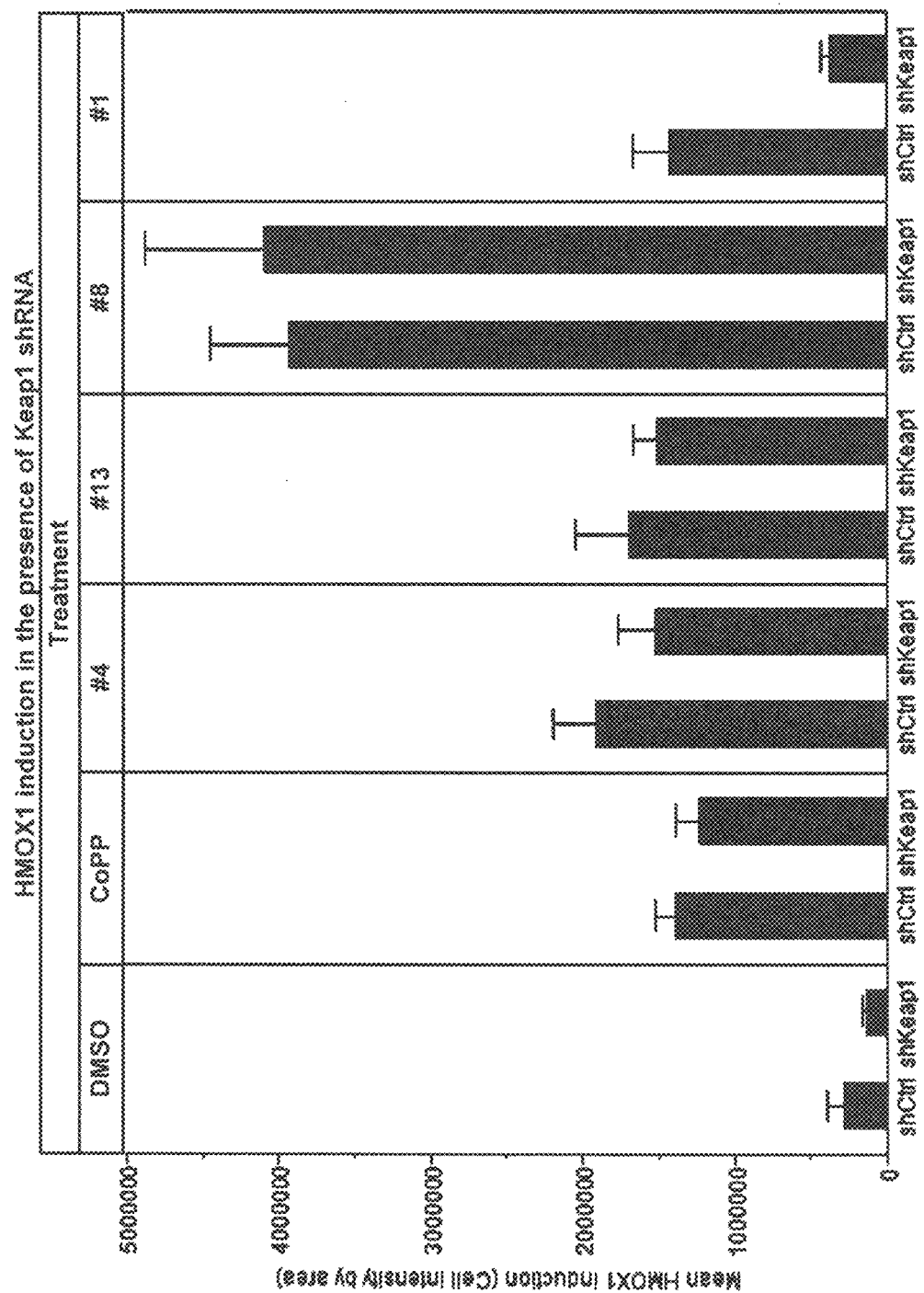
FIG. 6. Keap1 silencing has no effect on HMOX1 induction by Compound 13 and its analogues. NHLF cells treated with small hairpin RNA (shRNA) directed to Keap1 will suppress the induction of genes that require activation of Keap1 and increased levels of active Nrf2 for transcription. The tool compound CoPP activates HMOX1 transcription by direct depression of the transcriptional repressor Bach1. CoPP does not affect Keap1-Nrf2 directly as do agents that induce ROS.

Normal human lung fibroblasts were tested with DMSO, CoPP, Compound 13, and two derivatives including Compound 4 and Compound 8. An electrophile, Compound 1, was also included in the test set. As shown in FIG. 6, Keap1 silencing did not elevate HMOX1 levels in control NHLF cells. This is consistent with literature data showing that liver selective gene knockout of Keap1 does not elevate HMOX1 to a significant level. Addition of a test compound showed clear differences in effect of Keap1 silencing. Compound 13 and its two analogues as well as CoPP were unaffected in their ability to induce HMOX1 in the presence of Keap1 silencing. On the other hand, induction of HMOX1 by the electrophile Compound 1 was inhibited. This indicates that Compound 13 and analogues are able to affect HMOX1 production in the absence of an intact Keap1-Nrf2 regulatory circuit.

Figure 7:
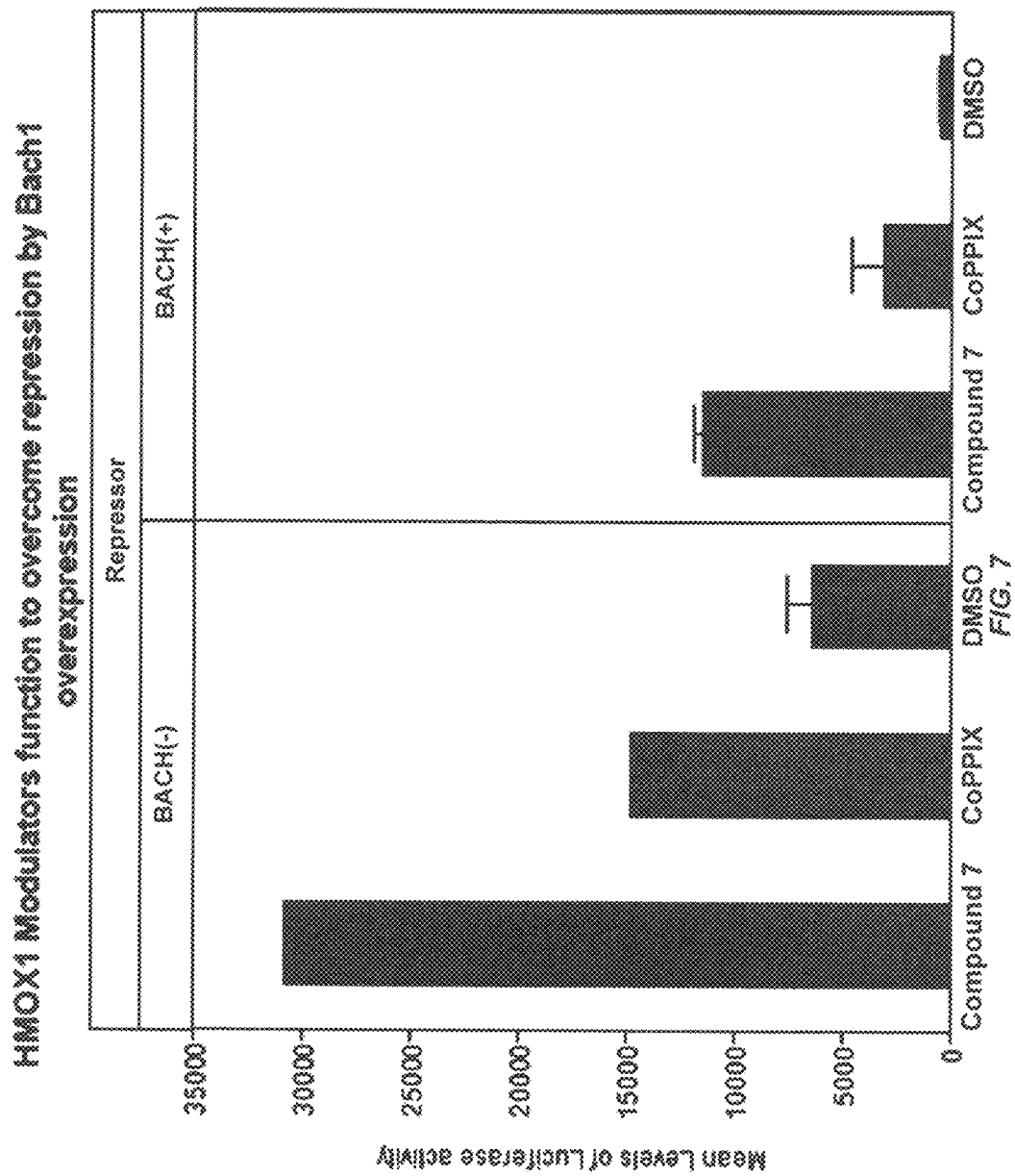
FIG. 7. Maf-anti-oxidant response element (MARE) controlled reporter gene assay in HepG2 cells demonstrates the effect of compounds that modulate oxidative stress response genes. MARE sequences are regulated by the presence of Bach1 and Nrf2.

The ability of Compound 13 to act in a manner similar to CoPP provides evidence for the hypothesis that Bach1 activity is being modulated by the compounds. As such, we attempted to ascertain whether we could demonstrate activity against Bach1 gene repression directly. To that end, expression vectors were prepared which contained the HMOX1 mARE promoter element recognized by both Bach1 and Nrf2. This element was placed in control of the reporter gene luciferase. Under conditions of transient transfection of HepG2 cells, the reporter has a low level of basal activity due to the relative ratio of Bach1 and Nrf2 found in the cell. Co-transfection with a Bach1 expressing plasmid leads to repression of luciferase activity. Therefore, one can test whether the compounds can increase the level of luciferase in the cells, thus overcoming Bach1 repression. As shown in FIG. 7, both CoPP and the Bach1 modulator Compound 7 are able to induce luciferase activity in the presence or absence of Bach1 protein expression. Thus, the tested compound is able to overcome suppression by additional Bach1. This demonstrates that the compounds may directly modulate Bach1 activity.

Example 2

Cellular Pharmacology, In Vivo Activity, and Pharmacokinetics of Bach1 Modulators Introduction After identification of Compound 13 as a useful lead with an appropriate transcriptional expression profile, the compound was optimized to have improved potency and more pharmaceutically acceptable properties. Structurally related analogues were synthesized using the primary screen and follow up transcript profiling was used to select compounds that had increased potency for HMOX1 gene induction. These compounds were tested in models of cellular efficacy. The compounds were also evaluated for metabolism, oral bioavailability, and in vivo activity.

Results

Figure 8A:
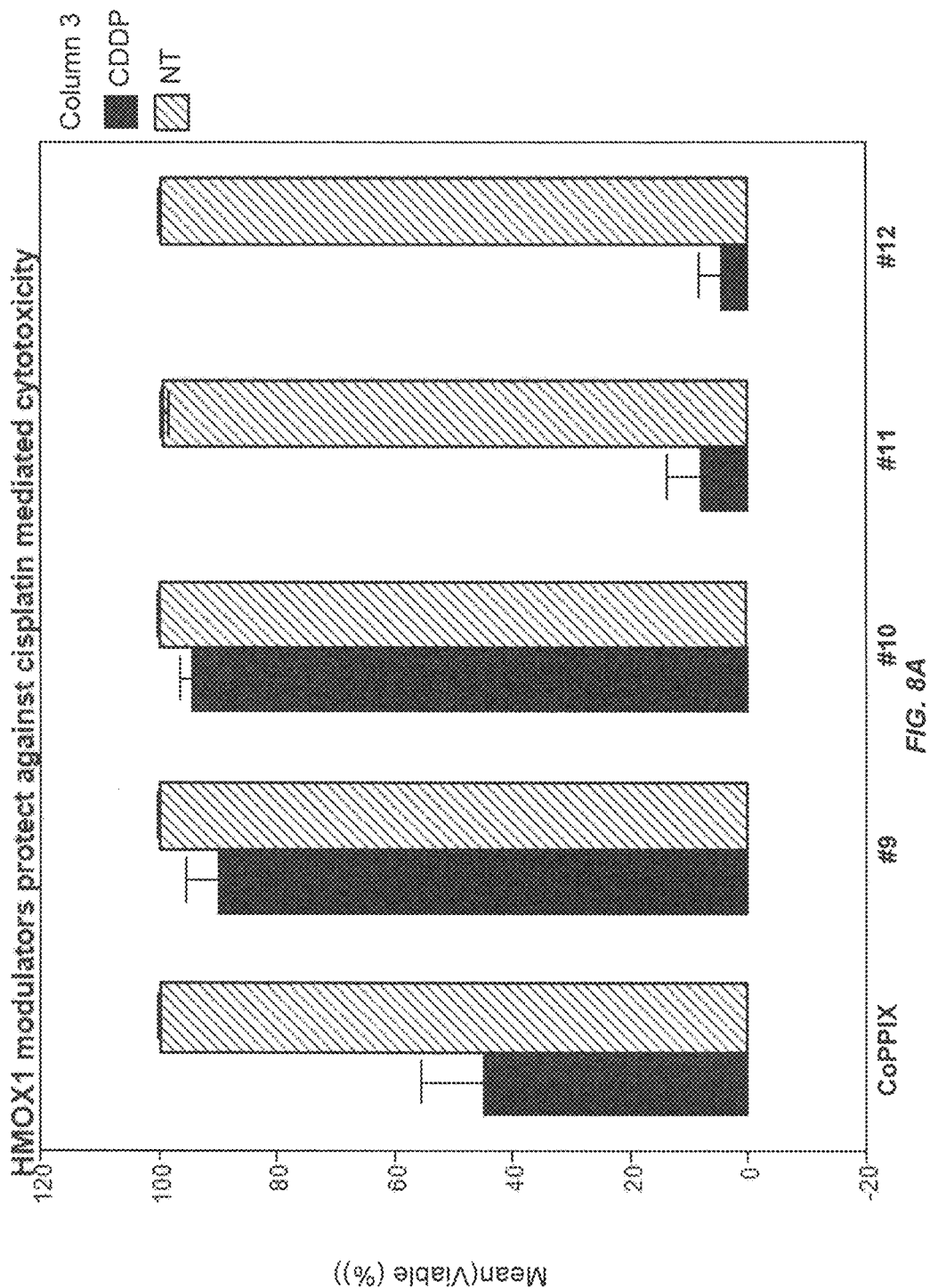
FIG. 8A is a graph showing percentage of viable NHLF cells following treatment with indicated compounds and then either cisplatin (CDDP) or no treatment (NT).
Figure 8B:
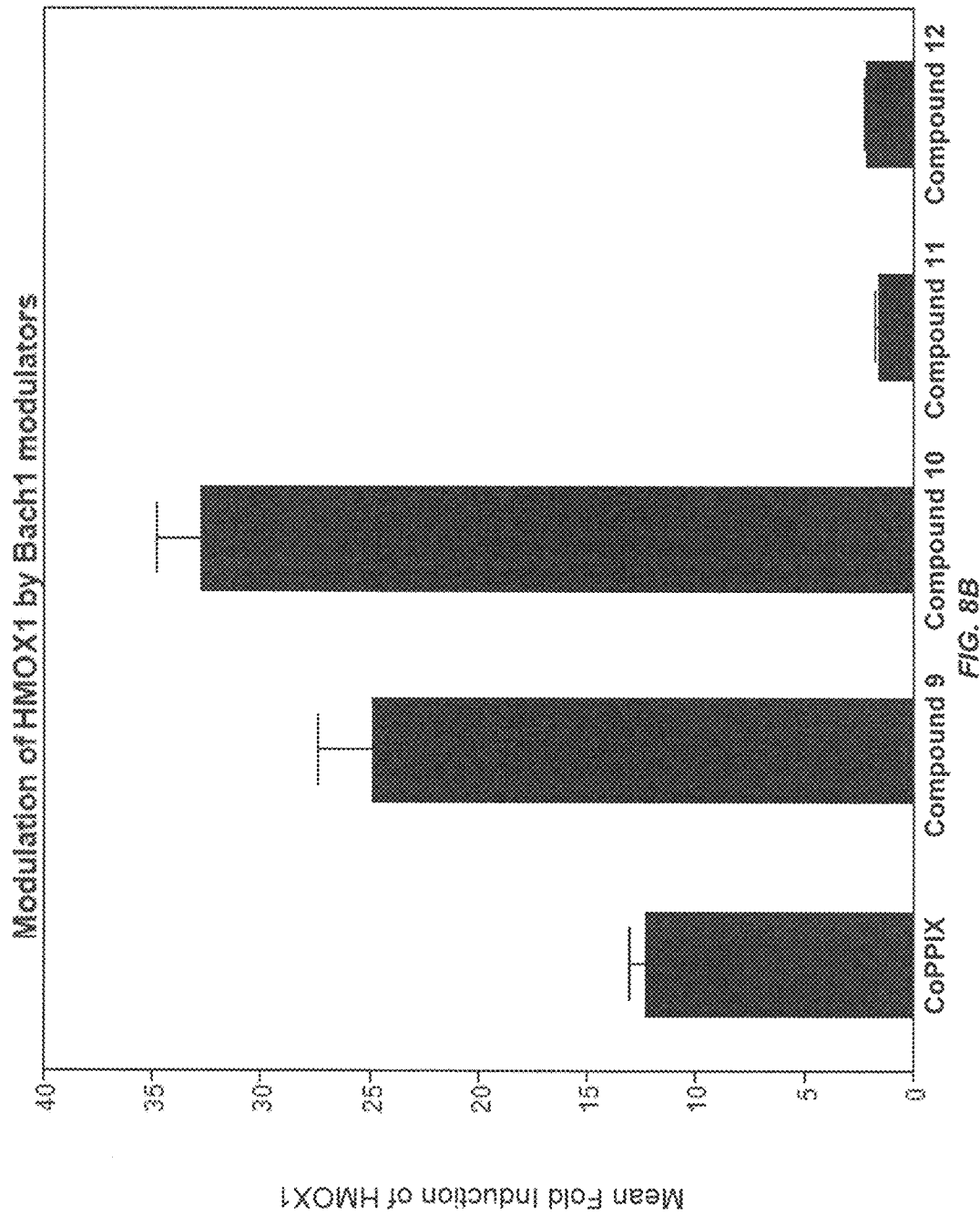
FIG. 8B is a graph showing mean fold induction of HMOX1 in NHLF cells following treatment with indicated compounds. Bach1 modulator-mediated cytoprotection in cisplatin (CDDP)-treated NHLF cells. NHLF cells treated with cisplatin (CDDP) will undergo apoptosis as measured by propidium iodide staining of the nucleus. A series of compounds were tested for their ability to protect the cells against cisplatin-mediated cytotoxicity. The tool compound CoPP and the test compounds Compound 9 and Compound 10 were demonstrated to protect the cells from CDDP-mediated toxicity (FIG. 8A) and did so in a manner that was consistent with the degree of HMOX1 induction (FIG. 8B). Compound 11 and Compound 12, which did not induce HMOX1, failed to protect cells from CDDP-mediated cytotoxicity.

A key outcome of Bach1 derepression and Nrf2 activation are the induction of cytoprotective genes. A method to test such cytoprotection is to assess the ability of a compound to protect normal human cells such as lung fibroblasts from toxicity due to cisplatin exposure. A model of cellular cytoprotection was established whereby normal human lung fibroblasts were treated with Bach1 modulators and then subsequently exposed to cisplatin. NHLF cells are very sensitive to cisplatin exposure; following a dose of 200 uM cisplatin, >90% of NHLF cells are propidium iodide positive, a measure of cell death. Addition of Bach1 modulators Compound 9 and Compound 10 24 hours prior to cisplatin exposure induced HMOX1 (FIG. 8A) and provided near-total cellular protection (FIG. 8B). However, Compound 11 and Compound 12, two related but inactive HMOX1 inducers, failed to protect NHLF cells against cisplatin toxicity.

Figure 9:
FIG. 9. HMOX1 can be induced by oxidative stress response compounds in human bone marrow-derived mesenchymal stem cells. Cells were cultured in the presence of Compound 9, Compound 12, or Compound 10 for 3 or 10 days. HMOX1 ("HO-1") induction was measured by Western blotting.

Previous work has shown that HMOX1 expression can suppress the differentiation of human bone marrow mesenchymal stem cells (BMMSC) into adipocytes, a process termed adipogenesis [Li et al., *Diabetes* 57(6):1526-1535 (2008)]. As such, we tested Bach1 modulators for the ability to suppress BMMSC differentiation into adipocytes in the presence of high glucose containing media. Two Bach1 modulators and a null compound were tested to determine the ability of the compounds to induce HMOX1 after 3 and 10 days of exposure to compound. In BMMSC, Compound 9 and Compound 10 induced HMOX1 as determined by Western blotting of cellular proteins, whereas the chemically related but inactive HMOX1 inducer Compound 12 failed to induce HMOX1 (FIG. 9).

Figure 10:
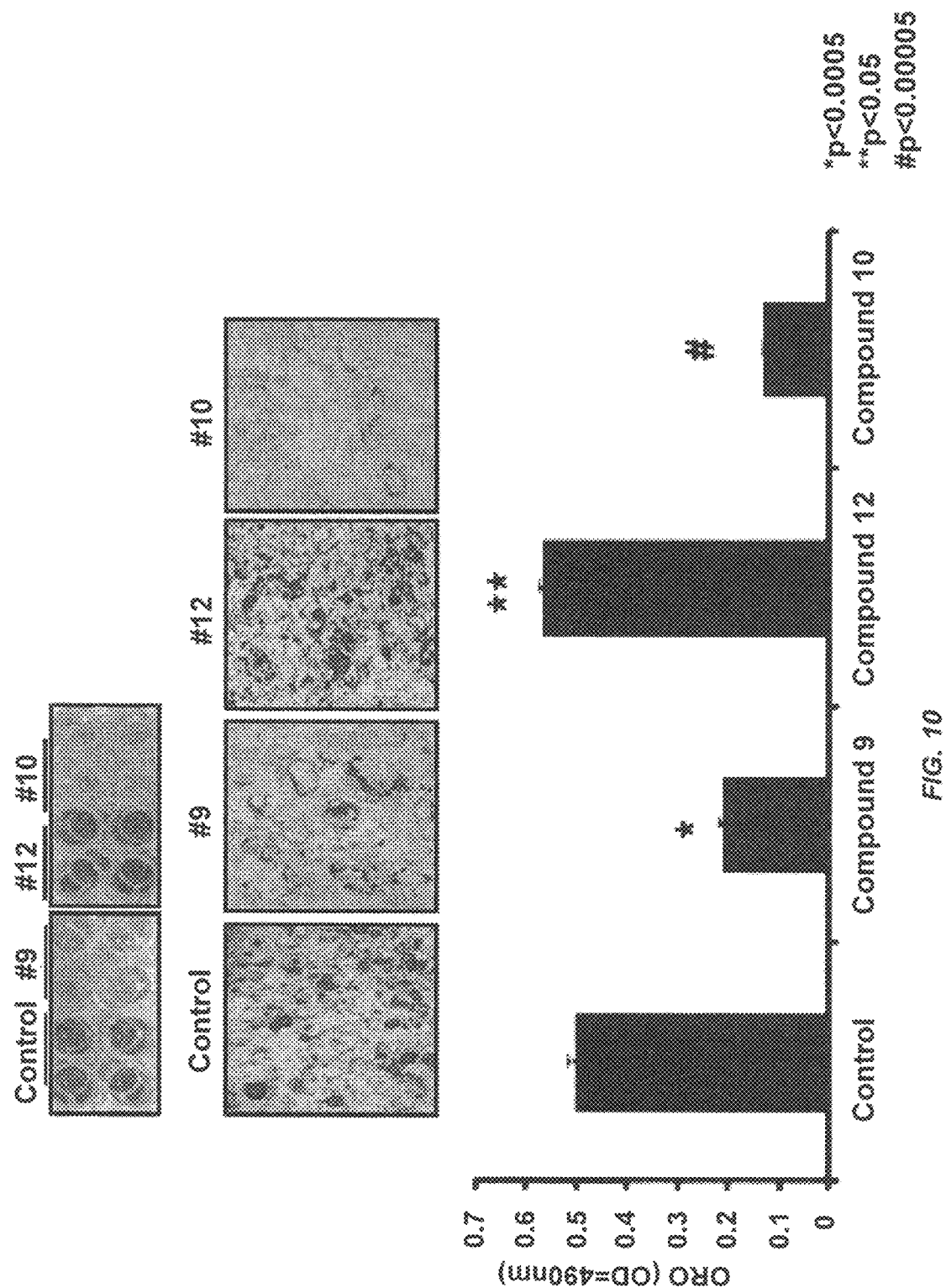
FIG. 10. Differentiation of human bone marrow-derived mesenchymal stem cells to adipocytes is inhibited by exposure to oxidative stress response compounds. Cells were cultured in the presence of Compound 9, Compound 12, or Compound 10 for 21 days. Differentiation of mesenchymal stem cells to adipocytes was monitored by Oil Red staining (top and middle panels) and quantified by absorbance (bottom panel). Compounds that induced HMOX1 (Compound 9 and Compound 10) inhibited stem cell differentiation, while a structurally related negative control (Compound 12) failed to do so.

An extended compound treatment of BMMSC in the presence of high glucose reveals the suppression of adipogenesis. In this assay, the cells are continuously exposed to compound for 21 days and then tested for the presence of oil-Red staining lipid droplets. As shown in FIG. 10, Compound 9 and Compound 10, compounds that induce HMOX1 (see FIG. 9), suppress Oil-O red staining, thus demonstrating an inhibition of stem cell differentiation to adipocytes. In contrast, Compound 12, which fails to induce HMOX1 (see FIG. 9), also fails to inhibit adipogenesis (FIG. 10).

Figure 11:
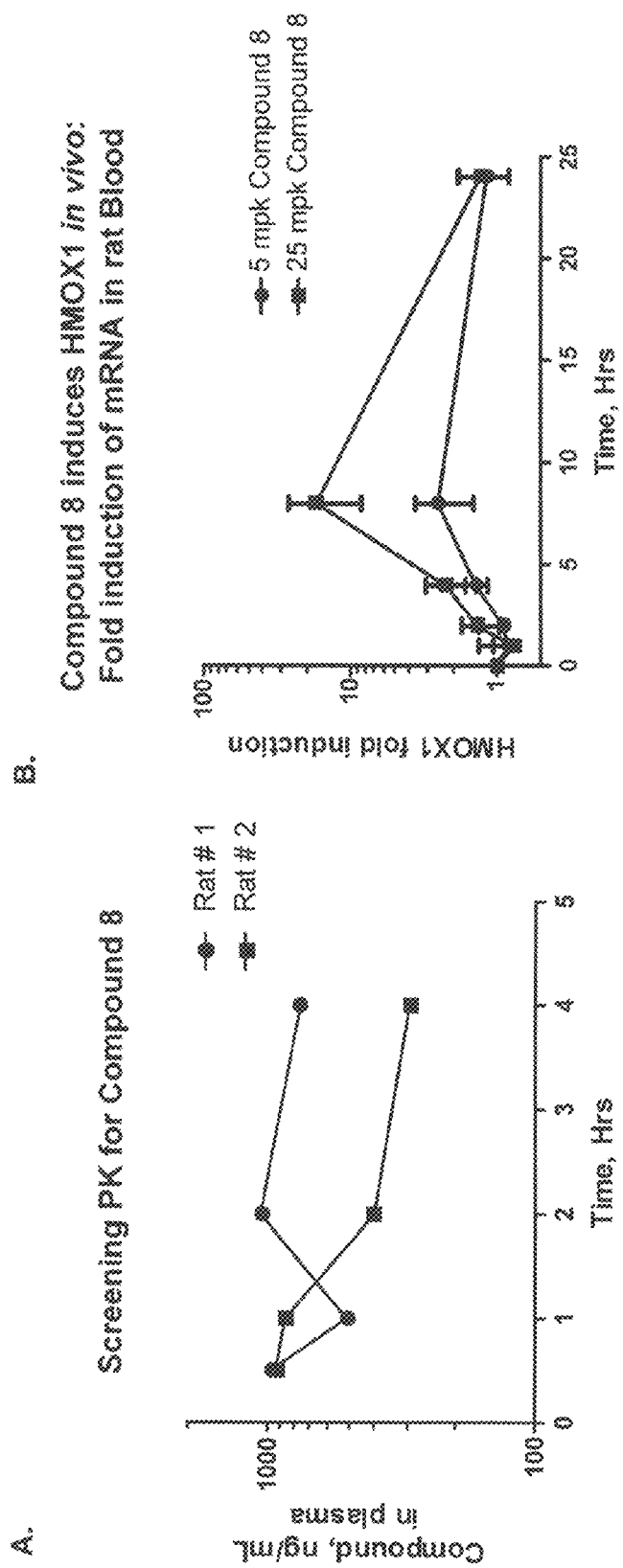
FIG. 11A is a graph showing blood plasma concentration of Compound 8 in rat over 5 hours.
FIG. 11B is a graph showing fold induction of HMOX1 in rat over 5 hours. Demonstration of oral bioavailability and in vivo activity of oxidative stress response inducers. Rats were dosed orally with 5 or 25 mg/kg of Compound 8 and blood samples were drawn at various time points. Compound 8 was present in blood sample following oral dosing (FIG. 11A) as determined by LC-MS quantization. Compound 8 was shown to be bioactive in rats as determined by dose-dependent induction of rat HMOX1 mRNA in blood samples (FIG. 11B).

Next, selected Bach1 modulators were tested for in vivo function. The Bach1 modulator Compound 8 was shown to be orally bioavailable and capable of inducing HMOX1 in rodents (FIG. 11). Rats were dosed with 5 mg/kg of compound by oral gavage. Compound levels in blood were determined by LC-MS (left panel). Compound 8 was shown to be present at micromolar levels in blood. In a second experiment, Compound 8 activity was tested by determining the amount of HMOX1 mRNA induced in rat blood. Animals were dosed by oral gavage and blood drawn at the indicated times. Compound 8 was able to induce HMOX1 mRNA in rat blood in a time and dose-dependent manner (right panel).

It is understood that the embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of selectively inducing an oxidative stress response in a cell, the method comprising:
    contacting a cell with a selective inducer compound,
        wherein the selective inducer compound
        i) is a non-naturally-occurring organic compound,
        ii) induces expression in the cell of at least the oxidative stress-responsive genes heme oxygenase 1 (HMOX1), NAD(P)H:quinine oxidoreductase (NQO1), and thioredoxin reductase 1 (TXNRD 1);
        iii) does not significantly activate the cellular stress response in the cell, wherein activation of the cellular stress response comprises inducing expression of at least the cellular stress genes Growth arrest and DNA-damage-inducible, alpha (GADD45A) and Heatshock 70kDa protein 6 (HSPA6); and
        iv) does not significantly activate nuclear factor-kappaB (NF-κB) in the cell, wherein activation of NF-κB is determined by measuring the induction of expression of intercellular adhesion molecule (ICAM-1);
    wherein the cell is selected from the group consisting of a lymphocyte, a granulocyte, a monocyte, a macrophage, a mast cell, a thrombocyte, an erythrocyte, a megakaryocyte, a dendritic cell, a glial cell, a pneumocyte, a Clara cell, a goblet cell, a myocardiocyte, a pericyte, a hepatocyte, a Kupffer cell, a Paneth cell, an osteoblast, an osteocyte, a chondroblast, a chondrocyte, a keratinocyte, a melanocyte, a myocyte, an adipocyte, a fibroblast, a tendon cell, an epithelial cell, an endothelial cell, a smooth muscle cell, a skeletal muscle cell, an embryonic stem cell, a neural stem cell, a skin stem cell, a mesenchymal stem cell, a hematopoietic stem cell, a stromal stem cell, and an epithelial stem cell.

2. The method of claim 1, wherein the cell is a mesenchymal stem cell, an osteocyte, or a chondrocyte.

3. The method of claim 1, where the contacting occurs in vivo in a mammalian subject.

4. The method of claim 1, where the contacting occurs ex vivo.

5. The method of claim 1, wherein the selective inducer compound induces expression of at least one oxidative stress-responsive gene in the cell by at least about two-fold as compared to an untreated cell, wherein the oxidative stress-response gene is selected from the group consisting of heme oxygenase 1 (HMOX1), NAD(P)H:quinine oxidoreductase (NQO1), and thioredoxin reductase 1 (TXNRD1).

6. The method of claim 1, wherein the selective inducer compound does not significantly increase reactive oxygen species (ROS) production in the cell.

7. The method of claim 1, wherein the selective inducer compound does not significantly decrease the level of glutathione in the cell.

* * * * *